(12) United States Patent
Jannes et al.

(10) Patent No.: US 7,455,970 B2
(45) Date of Patent: Nov. 25, 2008

(54) MUTATION ASSOCIATED WITH STROKES

(75) Inventors: Jim Jannes, Underdale (AU); Monica Anne Hamilton-Bruce, Woodville South (AU); Simon Koblar, Millswood (AU)

(73) Assignees: The Queen Elizabeth Hospital Research Foundation Inc., Woodville South (AU); Adelaide Research & Innovation Pty Ltd, Adelaide (AU)

(*) Notice: Subject to any disclaimer, the term of this patent is extended or adjusted under 35 U.S.C. 154(b) by 0 days.

(21) Appl. No.: 10/563,360

(22) PCT Filed: Jul. 2, 2004

(86) PCT No.: PCT/AU2004/000905

§ 371 (c)(1),
(2), (4) Date: Aug. 18, 2006

(87) PCT Pub. No.: WO2005/003382

PCT Pub. Date: Jan. 13, 2005

(65) Prior Publication Data

US 2007/0105110 A1    May 10, 2007

(30) Foreign Application Priority Data

Jul. 4, 2003    (AU) .............................. 2003903412

(51) Int. Cl.
C12Q 1/68 (2006.01)
C07H 21/04 (2006.01)
C07K 14/745 (2006.01)

(52) U.S. Cl. .............. 435/6; 536/23.2; 530/380
(58) Field of Classification Search .............. 435/6; 536/23.2; 530/380
See application file for complete search history.

(56) References Cited

FOREIGN PATENT DOCUMENTS

WO    WO-97/07240 A    2/1997

OTHER PUBLICATIONS

Degen et al., "The human tissue plasminogen activator gene," J Biol Chem 261(15):6972-6985, 1986.*
Bulens et al., "Rentinoic acid induction of human tissue-type plasminogen activator gene expression via a direct repeat element (DR5) located at −7 kilobases," J Biol Chem 270(13):7167-7175, 1995.*
Benza, RL et al. (1998), J. Thrombosis Thrombolysis 5, 143-50.
Austin, H et al., (2002) Stroke 33, 2762-9.
Iacoviello L et al. (1995), Fibrinolysis 10 (Supple 2), 13-6.
Bang C-O et al. (2001), Cerebrovascular Disease 11, 294-9.
Tabrizi, P et al., (1999) Arterioscler Thromb Vasc Biol 19, 2801-6.

* cited by examiner

*Primary Examiner*—Rebecca E. Prouty
*Assistant Examiner*—Rosanne Kosson
(74) *Attorney, Agent, or Firm*—Birch, Stewart, Kolasch & Birch, LLP

(57) ABSTRACT

The present invention relates to a method of identifying a subject predisposed to ischemic stroke. The method includes the step of identifying a mutation in the subject that reduces the release rate of tissue plasminogen activator.

5 Claims, 2 Drawing Sheets

```
ttaagcccat caatccaatc ggtgactaaa atcagacagg aagccctgtg cccCttagat    1800
                     Consensus primer          attggcgcaa actcctcaca
aaagaaagcc tggggggaaa atgatctcaa gttcatttcg attggcgcaa actcctcaca    1860
gaggaaaaaa tgtacagtta gagtgaagtg aaagaacatc tctataaaat atgcatcact    1920
tcctggcggg gaggagagag gagctatgga aagctacacc aaagctgtat tcactggaca    1980
aaaatgcttg actcaggaag gaggccggag cggcgagtcc tgtgatgcca tggcgggagg    2040
tgggtcccat gtaaacagtg gtgttcctgt cacCctgagc acatgcagtc tcccgtgggt    2100
aaccagaact gatgcaagag cccctgctgt ggaagtcacc acgctctccc agaacgcgcc    2160
tcccCccagg tctgagtgat ctcattgccg aggtgaatag ggctttggcc gctctcccaa    2220
aggagccCgc cccagacaca gccatggcct gggactctgg ggtcaccctg gggtcagaag    2280
    gcg gggtctgtgt cggta      WT Primer
    acg gggtctgtgt cggta      SNP Primer
gaattatctg tattcacttg gttttggtta ttgtcagtgt tatttatgtg tttatttatt    2340 tttattttt agagacaggc ttttactctg tctcccaggc tggagtgcag tgatgggatc    2400
```

Figure 1

```
ttaagcccat caatccaatc ggtgactaaa atcagacagg aagccctgtg ccccttagat   1800
                     Consensus primer       attggcgcaa actcctcaca
aaagaaagcc tgggggaaa atgatctcaa gttcatttcg attggcgcaa actcctcaca    1860
gaggaaaaaa tgtacagtta gagtgaagtg aaagaacatc tctataaaat atgcatcact   1920
tcctggcggg gaggagagag gagctatgga aagctacacc aaagctgtat tcactggaca   1980
aaaatgcttg actcaggaag gaggccggag cggcgagtcc tgtgatgcca tggcgggagg   2040
tgggtcccat gtaaacagtg gtgttcctgt caccctgagc acatgcagtc tcccgtgggt   2100
aaccagaact gatgcaagag cccctgctgt ggaagtcacc acgctctccc agaacgcgcc   2160 tcccccagg tctgagtgat ctcattgccg aggtgaatag ggctttggcc gctctcccaa    2220
aggagccCgc cccagacaca gccatggcct gggactctgg ggtcaccctg gggtcagaag   2280
       gcg gggtctgtgt cggta       WT Primer
       acg gggtctgtgt cggta       SNP Primer
gaattatctg tattcacttg gttttggtta ttgtcagtgt tatttatgtg tttatttatt   2340
ttttattttt agagacaggc ttttactctg tctcccaggc tggagtgcag tgatgggatc   2400
```

MUTATION ASSOCIATED WITH STROKES

This application is the U.S. national phase of International Application No. PCT/AU04/00905,filed on Jul. 2, 2004, which claims priority to Australian Application No. 2003-903412, filed on Jul. 4, 2003.

FIELD OF THE INVENTION

The present invention relates to methods of identifying subjects having a predisposition to ischemic stroke.

BACKGROUND OF THE INVENTION

Ischemia occurs when there is an imbalance between oxygen supply and demand, leading to an insufficient supply of oxygen to a tissue or organ. Ischemia often occurs as the result of the formation of a blood clot (thrombus) in a vessel which then obstructs the flow of blood in the vessel.

In ischemic strokes an occlusive thrombus forms in one of the vessels of the brain. Ischemic stroke may be thrombotic or embolic in origin. In a thrombotic stroke, a blood clot develops in a vessel already narrowed by atherosclerosis. In an embolic stroke, a clot forms elsewhere in the body and travels through the circulatory system to the brain.

Lacunar strokes, which are strokes due to the blockage of small arteries in the brain, may be thrombotic or embolic in origin. In some cases lacunar strokes can also arise from causes other than arteriosclerosis, such as lipohyalinosis.

The likelihood of a clot forming in a vessel is determined by the balance between the coagulation cascade, which favours clot formation, and the fibrinolytic system, which favours lysis of the clot. Both the coagulation cascade and the fibrinolytic system involve a complex cascade of proteolytic events. The final effector molecule of the coagulation cascade is the serine protease thrombin, which cleaves fibrinogen to form the fibrin clot. The final effector molecule of the fibrinolytic system is the serine proteinase plasmin, which cleaves fibrin into soluble degradation products.

Tissue plasminogen activator (tPA) plays a critical role in the fibrinolytic system. tPA catalyses the conversion of the inactive precursor plasminogen into the active proteinase plasmin. As such, tPA is the primary mediator of intravascular fibrinolysis preventing thrombosis. The secretion of tPA by endothelial cells is regulated by two mechanisms: (a) an acute release of local tPA that is precipitated by vascular injury and occurs within seconds to minutes and (b) a long-term basal secretion rate that is determined by the chronic activation of the fibrinolytic system and is responsible for the changes in the circulating plasma level of tPA. The circulating tPA activity is also attenuated through the formation of an irreversible complex with plasminogen activator inhibitor-1. A variety of stimuli such as venous occlusion, exercise, or injection of vasoactive substances are known to acutely increase plasma levels of t-PA by stimulating release of tPA.

Activation of the fibrinolytic system does not necessarily correlate with a reduced probability of suffering an ischemic stroke. Indeed, in some cases prolonged activation of the fibrinolytic defense system appears to precede a stroke event by several years.

There is currently very little information regarding the importance that genetic factors play in the development of diseases and conditions associated with occlusive thrombosis, and in particular, the genetic factors that play a role in ischemic stroke. As such, there is a need for methods of identifying subjects that may be susceptible to occlusive thrombosis, including methods for identifying subjects that are susceptible to ischemic stroke.

The present invention relates to methods of identifying subjects predisposed to ischemic stroke by identifying a mutation in the subject that reduces the rate of release of tissue plasminogen activator. In particular, the present invention relates to the identification that the presence of a specific polymorphism in the upstream region of the tPA gene is associated with ischemic stroke. This polymorphism is associated with a reduced rate of release of tPA. Throughout this specification reference may be made to documents for the purpose of describing various aspects of the invention. However, no admission is made that any reference cited in this specification constitutes prior art. In particular, it will be understood that the reference to any document herein does not constitute an admission that any of these documents forms part of the common general knowledge in the art in Australia or in any other country. The discussion of the references states what their authors assert, and the applicant reserves the right to challenge the accuracy and pertinency of any of the documents cited herein.

SUMMARY OF THE INVENTION

The present invention provides a method of identifying a subject predisposed to ischemic stroke, the method including the step of identifying a mutation in the subject that reduces the release rate of tissue plasminogen activator.

The present invention provides a method of identifying a subject predisposed to small vessel occlusion, the method including the step of identifying a mutation in the subject that reduces the release rate of tissue plasminogen activator.

The present invention also provides a method of identifying a subject predisposed to a disease or condition associated with small vessel occlusion, the method including the step of identifying a mutation in the subject that reduces the release rate of tissue plasminogen activator.

The present invention also provides a method of identifying a subject suitable for intervention to prevent and/or treat ischemic stroke, the method including the step of identifying a mutation in the subject that reduces the release rate of tissue plasminogen activator.

The present invention also provides a method of identifying a subject suitable for intervention to prevent and/or treat a small vessel occlusion or disease or condition associated with small vessel occlusion, the method including the step of identifying a mutation in the subject that reduces the release rate of tissue plasminogen activator.

The present invention also provides a method of treating a disease or condition associated with small vessel occlusion in a subject, the method including the step of administering to the subject a therapeutically effective amount of an agent that increases the rate of release of tissue plasminogen activator in the subject.

The present invention also provides a method of identifying an agent capable of increasing the release rate of tissue plasminogen activator from a cell, the method including the steps of:
(a) exposing an agent to a cell including a mutation that decreases the release rate of tissue plasminogen activator from the cell;
(b) determining the release rate of tissue plasminogen activator from the cell so exposed to the agent; and
(c) identifying the agent as an agent capable of increasing the release rate of tissue plasminogen activator from the cell.

The present invention further provides a method of identifying a subject predisposed to ischemic stroke, the method including the step of identifying in the subject the presence of a cytosine to thymine mutation at position −7351 in both alleles of the tissue plasminogen activator locus.

The present invention also provides a method of identifying a subject predisposed to a small vessel occlusion or disease or condition associated with small vessel occlusion, the method including the step of identifying in the subject the presence of a cytosine to thymine mutation at position −7351 in both alleles of the tissue plasminogen activator locus.

The present invention also provides a method of identifying a subject suitable for intervention to prevent and/or treat ischemic stroke, the method including the step of identifying in the subject the presence of a cytosine to thymine mutation at position −7351 in both alleles of the tissue plasminogen activator locus.

The present invention also provides a method of identifying a subject suitable for intervention to prevent and/or treat a small vessel occlusion or disease or condition associated with small vessel occlusion, the method including the step of identifying in the subject the presence of a cytosine to thymine mutation at position −7351 in both alleles of the tissue plasminogen activator locus.

The present invention also provides a method of identifying a subject suitable for treatment with an agent that increases the rate of release of tissue plasminogen activator, the method including the step of identifying in the subject the presence of a cytosine to thymine mutation at position −7351 in both alleles of the tissue plasminogen activator locus.

The present invention also provides a method of determining the risk of ischemic stroke in a subject, the method including the step of determining the presence in the subject of a cytosine to thymine mutation at position −7351 in one or both alleles of the tissue plasminogen activator locus.

The present invention also provides a method of determining the risk of small vessel occlusion in a subject, or the risk of developing a disease or condition associated with small vessel occlusion in a subject, the method including the step of determining the presence in the subject of a cytosine to thymine mutation at position −7351 in one or both alleles of the tissue plasminogen activator locus.

The present invention further provides a method of identifying an agent capable of altering the release rate of tissue plasminogen activator from a cell, the method including the steps of:
  (a) exposing an agent to a cell including a cytosine to thymine polymorphism at position −7351 in one or both alleles of the tissue plasminogen activator locus;
  (b) determining the release rate of tissue plasminogen activator from the cell so exposed to the agent; and
  (c) identifying the agent as an agent capable of altering the release rate of tissue plasminogen activator from the cell.

The present invention further provides a method of identifying an agent capable of increasing the release rate of tissue plasminogen activator from a cell, the method including the steps of:
  (a) exposing an agent to a cell transformed with all or part of the tissue plasminogen activator locus, wherein the transformed locus includes a cytosine to thymine mutation at position −7351 and the transformed locus regulates expression of a reporter gene;
  (b) determining the level of expression of the reporter gene in the cell so exposed to the agent;
  (c) identifying an agent capable of increasing the expression of the reporter gene; and
  (d) identifying the agent capable of increasing the expression of the reporter gene as an agent capable of increasing the release rate of tissue plasminogen activator from a cell.

The present invention also provides an isolated nucleic acid consisting of the sequence according to SEQ. ID No. 3 or RNA equivalent thereof.

The present invention also provides an isolated nucleic acid with one or more base substitutions in the sequence according to SEQ ID No. 3, wherein the nucleic acid hybridises with the complement of SEQ ID No. 3 under stringent hybridisation conditions and the stringent hybridisation conditions include hybridisation in 6× SSC at 42° C. and washing in 2× SSC at 20° C.

The present invention also provides an isolated nucleic acid consisting of the sequence according to SEQ. ID No. 4 or RNA equivalent thereof.

The present invention also provides an isolated nucleic acid with one or more base substitutions in the sequence according to SEQ ID No. 4, wherein the nucleic acid hybridises with the complement of SEQ ID No. 4 under stringent hybridisation conditions and the stringent hybridisation conditions include hybridisation in 6× SSC at 42° C. and washing in 2× SSC at 20° C.

The present invention also provides an isolated nucleic acid with one or more base substitutions in the sequence according to SEQ ID No. 3, wherein the nucleic acid has at least 80% homology to SEQ. ID No. 3 or RNA equivalent thereof.

The present invention also provides an isolated nucleic acid with one or more base substitutions in the sequence according to SEQ ID No. 4, wherein the nucleic acid has at least 80% homology to SEQ. ID No. 4 or RNA equivalent thereof.

The present invention also provides an isolated nucleic acid, the nucleic acid consisting of the sequence spanning nucleotides 1840 to 2245 of SEQ ID No. 1.

The present invention also provides a method of identifying a subject predisposed to ischemic stroke, the method include the step of identifying a reduced rate of release of tissue plasminogen activator in the subject.

The present invention also provides a method of identifying a subject predisposed to a small vessel occlusion, the method including the step of identifying a reduced rate of release of tissue plasminogen activator in the subject.

The present invention also provides a method of identifying a subject predisposed to a disease or condition associated with small vessel occlusion, the method including the step of identifying a reduced release rate of tissue plasminogen activator in the subject.

The present invention also provides a method of identifying a subject suitable for intervention to prevent and/or treat ischemic stroke, the method including the step of identifying a reduced release rate of tissue plasminogen activator in the subject.

The present invention also provides a method of identifying a subject suitable for intervention to prevent and/or treat a small vessel occlusion or a disease or condition associated with small vessel occlusion, the method including the step of identifying a reduced release rate of tissue plasminogen activator in the subject.

The present invention arises out of studies into the predisposition to ischemic strokes in humans. In particular, it has been found that a mutation in an enhancer of the tissue plasminogen activator gene is an independent prognostic indicator for ischemic stroke. This finding indicates that a reduced release rate of tissue plasminogen in an individual is an independent prognostic indicator for ischemic stroke.

Various terms that will be used throughout the specification have meanings that will be well understood by a skilled addressee. However, for ease of reference, some of these terms will now be defined.

The term "tPA locus" as used throughout the specification is to be understood to mean any DNA associated with the coding region of the tPA gene, any DNA coding for an untranslated region of a tPA mRNA, any DNA coding for a tPA pre-mRNA (eg intronic sequences) or any DNA associated with the regulation of tPA expression, such as a promoter element, an enhancer element (proximal or distal), a binding site for a regulatory factor (eg a SP1 binding site) or any other DNA that has a role in expression of the tPA locus, such as heterochromatic DNA. The term "predisposed" as used throughout the specification in relation to ischemic stroke or small vessel occlusion is to be understood to mean the increased probability that a subject with a mutation will suffer an ischemic stroke or a small vessel occlusion, as compared to the probability that another subject not having the mutation will suffer an ischemic stroke or a small vessel occlusion, under circumstances where other risk factors (eg atrial fibrillation, history of smoking) for having an ischemic stroke or a small vessel occlusion between the subjects are the same.

The term "mutation" as used throughout the specification is to be understood to mean any change in the normal DNA sequence. As will be appreciated a mutation will also be polymorphic. Examples of types of mutations include an insertion, deletion, frameshift, or base substitution.

The term "small vessel occlusion" as used throughout the specification is to be understood to mean the occlusion by thrombus of any blood vessel less than 800 micrometres in diameter. The definition includes pre-capillary arterioles, capillaries and post-capillary venules. Within the brain, small vessel occlusion may manifest clinically as lacunar stroke, thalamic infarction, white matter medullary infarction or generalized subcortical leukoariosis. The latter pathological entity underlies vascular dementia.

A "polymorphism" as used throughout the specification is to be understood to mean a difference in DNA sequence among individuals.

The terms "amplification" or "amplify" (or variants thereof) as used throughout the specification is to be understood to mean the production of additional copies of a nucleic acid sequence. For example, amplification may be achieved using polymerase chain reaction (PCR) technologies (as described in Dieffenbach, C. W. and G. S. Dveksler (1995) PCR Primer, a Laboratory Manual, Cold Spring Harbor Press, Plainview, N.Y.) or by other methods of amplification, such as rolling circle amplification on circular templates, such as described in Fire, A. and Xu, S-Q. (1995) *Proc. Natl. Acad. Sci* 92: 4641-4645.

The term "nucleic acid" as used throughout the specification is to be understood to mean any polynucleotide or oligonucleotide, being composed of deoxyribonucleotides or ribonucleotides in either single- or double-stranded form, including known analogues of natural nucleotides that can function in a similar manner as naturally occurring nucleotides.

In this regard, the nucleic acid may be modified at the base moiety, sugar moiety, or phosphate backbone, and may include other appending groups to facilitate the function of the nucleic acid.

For example, the nucleic acid may include at least one modified base moiety which is selected from the group including 5-fluorouracil, 5-bromouracil, 5-chlorouracil, 5-iodouracil, hypoxanthine, xanthine, 4-acetylcytosine, 5-(carboxyliydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil5-oxyacetic acid methylester, uracil-5-oxyacetic acid (v), 5-methyl-2-thiouracil, 3- (3-amino-3-N-2-carboxypropyl) uracil, (acp3) w, and 2,6-diaminopurine.

The nucleic acid may also include at least one modified sugar moiety selected from the group including, but not limited to, arabinose, 2-fluoroarabinose, xylulose, and hexose. In addition, the nucleic acid may include at least one modified phosphate backbone, such as a phosphorothioate, a phosphorodithioate, a phosphoramidothioate, a phosphoramidate, a phosphordiamidate, a methylphosphonate, an alkyl phosphotriester, a formacetal or any analogue thereof.

The term "isolated nucleic acid" as used throughout the specification is to be understood to mean a nucleic acid which is substantially separated from other cellular components which naturally accompany the nucleic acid. The term includes a nucleic acid sequence which has been removed from its naturally occurring environment, and includes natural, cloned or recombinant DNAs, chemically synthesized nucleic acids, such as chemically synthesized oligonucleotides, any DNA or RNA biologically synthesized by a heterologous system, or any other form of polynucleotide analogue.

The term "hybridises" or "hybridisation" (or variants thereof) as used throughout the specification is to be understood to mean any process by which a strand of nucleic acid binds with a complementary strand through base pairing. Hybridisation may occur in solution, or between one nucleic acid sequence present in solution and another nucleic acid sequence immobilized on a solid support (e.g., membranes, filters, chips etc).

The term "stringent conditions" as used throughout the specification is to be understood to mean the conditions that allow complementary nucleic acids to bind to each other within a range from at or near the Tm (Tm is the melting temperature) to about 20° C. below Tm. Factors such as the length of the complementary regions, type and composition of the nucleic acids (DNA, RNA, base composition), and the concentration of the salts and other components (e.g. the presence or absence of formamide, dextran sulfate and/or polyethylene glycol) must all be considered, essentially as described in in Current Protocols in Molecular Biology, John Wiley & Sons, N.Y. (1989).

The term "upstream region" in relation to the tPA locus as used throughout the specification will be understood to mean those sequences normally within 10 kb of the start of the transcribed region of the tPA locus (but which may also be more distant from the coding region), which affect the expression of the gene (including transcription of the gene, and translation, splicing, stability or the like of the messenger RNA).

In this regard, sequence coordinates used throughout the specification in relation to the upstream region of the tPA locus correspond to the sequence coordinates of GenBank Accession No. Z48484.

BRIEF DESCRIPTION OF THE FIGURES

FIG. 1 shows the nucleotide sequence (nucleotides 1750 to 2400 of SEQ ID NO: 1) of the upstream region of the tissue plasminogen activator locus in the vicinity of the -7351 C/T polymorphism. The nucleotide sequence coordinates are based on GenBank Accession No. Z48484. The position of the C/T polymorphism at nucleotide 2228 is shown in bold. Positions of Consensus primer (SEQ ID No. 2; nucleotides 1840-1860), WT primer (SEQ ID No. 3; nucleotides 2245-2228) and SNP primer (SEQ ID No. 4; nucleotides 2245-2228) are also shown.

GENERAL DESCRIPTION OF THE INVENTION

Figure 2:
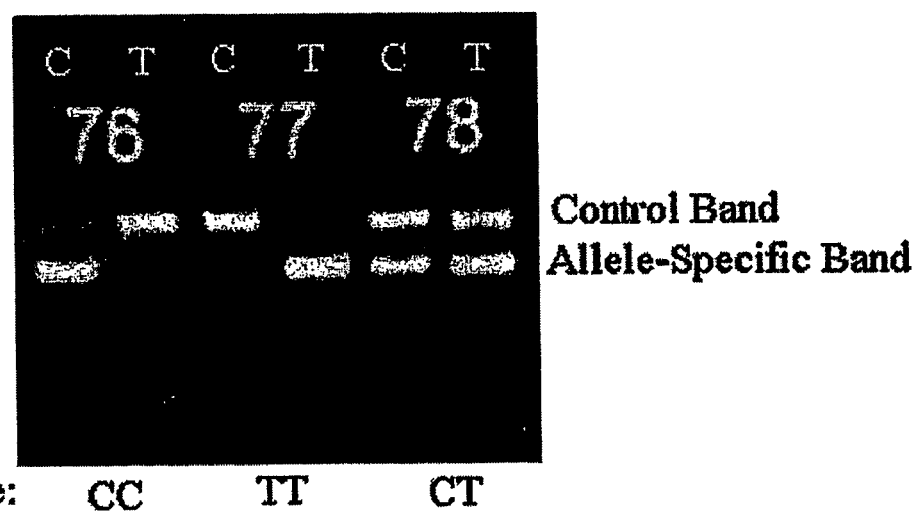
FIG. 2 shows results of agarose gel electrophoresis of the amplification products from three subjects of different tPA genotype.

As mentioned above, in one form the present invention provides a method of identifying a subject predisposed to ischemic stroke, the method including the step of identifying a mutation in the subject that reduces the release rate of tissue plasminogen activator.

The subject is any human subject of either gender for which the predisposition to ischemic stroke is to be determined. Preferably, the subject is a human of Caucasian origin.

The ischemic stroke is any thrombotic or embolic stoke that may occur in the subject, including a cardioembolic or atherothrombotic ischemic stroke. Preferably, the ischemic stroke is an atherothrombotic ischemic stroke.

Preferably, the ischemic stroke is a small vessel stroke (ie a lacunar stroke). Accordingly, in a preferred form, the present invention provides a method of identifying a subject predisposed to lacunar stroke, the method including the step of identifying a mutation in the subject that reduces the release rate of tissue plasminogen activator.

The mutation in the subject is any mutation in any gene or extragenic region that reduces the release rate of tPA from an endothelial cell. For example, the mutation may be in a gene or region not associated with the tPA locus, or be a mutation in the tPA locus, such as a mutation in a region upstream of the tPA coding region that affects transcription of the tPA gene, a mutation in an enhancer, a mutation in an exon of the tPA gene, a mutation in an intron that affects splicing, or a mutation in the 3' region of the tPA that affects translation or mRNA stability.

The mutation may be present in one or both alleles of the particular gene. Most preferably, the mutation is present in both alleles of the particular gene.

Preferably, the mutation is a mutation in the tPA locus. In a particularly preferred form, the mutation is in both alleles of the tPA locus.

In this regard, the structure of the human tPA locus is as described in Degen et aL (1986) *J. Biol. Chem.* 261(15):6972-6985. The tPA gene consists of 14 exons and 13 introns.

The upstream region includes a number of regions that act to regulate transcription of the gene. For example, transcription of the human tPA gene is regulated by a multi-hormonal responsive enhancer at −7 kb, and transient transfection studies have shown that tPA reporter constructs having the −7 kb enhancer require SP1 binding in the proximal promoter region allow induction of the promoter by retinoic acid mediated by the enhancer.

A C to T polymorphism at −7351 in the upstream region of tPA has been previously identified and this mutation reduces the release rate of tPA in vivo in individuals heterozygous and homozygous for the polymorphism (Ladenvall et al. (2000) *Thromb. Haemost.* 84: 150-155). This mutation is in an SP1 binding site.

The ability of a mutation to reduce the release rate of tissue plasminogen activator may be determined by a suitable method known in the art. For example, the ability of specific mutation to reduce the release rate of tPA from endothelial cells may be determined by culturing endothelial cells in vitro carrying the mutation and determining the rate of release of tPA from the endothelial cells, by washing the cells with fresh medium and determining the extent of rate of change of tPA released into the medium over time, as compared to wild type endothelial cells. An enzyme-linked immunosorbent assay (ELISA) may be employed for the quantitative determination of total t-PA antigen (eg TintElize® t-PA, Biopool AB). Such assays are based on the double-antibody principle. Free t-PA and t-PA in complex with inhibitors are detected with equal efficiency.

To induce release of tPA from the endothelial cells, agents known in the art that induce release of tPA may be utilised, such as thrombin or calcium ionophore. A suitable method for inducing the release of tPA from endothelial cells in vitro is as described in Rosnoblet et al. (1999) *Arterioscler Thromb Vasc Biol* 1 9(7):1 796-803.

Alternatively, the rate of release of tPA in a subject may be determined directly, for example by determination of forearm release rates as compared to a subject without the mutation. A suitable method for determining the rate of release of tPA in vivo is as described in Jern et al. (1999) *Arterioscler. Thromb. Vasc. Biol* 19(2): 454-459.

Preferably, the mutation is located in the tPA locus. More preferably, the mutation in the subject is a mutation in an upstream region of the tPA locus. More preferably, the mutation is a mutation in an enhancer element in the tPA locus. Most preferably, the mutation is a cytosine to thymine mutation at position −7351 of the upstream region of the tPA locus.

The −7351 cytosine to thymine mutation may be present in one or both alleles of the tPA locus. Most preferably, the mutation is present in both alleles of the tPA locus.

Accordingly, in a preferred form, the present invention provides a method of identifying a subject predisposed to ischemic stroke, the method including the step of identifying in the subject the presence of a cytosine to thymine mutation at position −7351 in both alleles of the tissue plasminogen activator locus.

As discussed previously, preferably the ischemic stroke is a lacunar stroke. Accordingly, in another preferred form, the present invention provides a method of identifying a subject predisposed to lacunar stroke, the method including the step of identifying in the subject the presence of a cytosine to thymine mutation at position −7351 in both alleles of the tissue plasminogen activator locus.

The identification of a mutation in the subject that reduces the release rate of tPA may be determined by a suitable method known in the art.

DNA may be isolated from the subject by a suitable method known in the art. A suitable method for isolating genomic DNA from a subject is from whole venous blood as described in Miller et al. (1988) *Nucleic Acids Research* 16(3):1215.

Various methods may be used to identify the mutation. DNA sequencing (either manual sequencing or automated fluorescent sequencing) can be used to detect the mutation. IL this case, identification of the mutation will usually involve amplification of the region containing the mutation from nucleic acid isolated from the subject (generally genomic DNA), although it is also possible to identify the mutation by sequencing a clone of the region derived from a particular subject, with or without amplification.

Another approach for identifying mutations is the single-stranded conformation polymorphism assay (SSCA) (as described in Orita et al. (1989) *Genomics* 5(4): 874-879. This method does not detect all sequence changes, especially if the DNA fragment size is greater than 200 bp, but can be optimized to detect most DNA sequence variation. Fragments which have shifted mobility on SSCA gels are then sequenced to determine the exact nature of the DNA sequence variation.

Another approach is based on the detection of mismatches between two complementary DNA strands, including clamped denaturing gel electrophoresis (as described in Sheffield et al. (1991) *Am. J. Hum. Genet.* 49:699-706), heteroduplex analysis (as described in White et al. (1992) *Genomics* 12:301-303) and chemical mismatch cleavage (as described in Grompe et al. (1989) *Proc. Natl. Acad. Sci. USA* 86:5855-5892). Once a specific mutation is identified, an allele specific detection approach such as allele specific oligonucleotide hybridization can be utilized.

If DNA sequence analysis is used to identify a mutation, the presence of a mutation in one allele (ie the subject is heterozygous for the mutation) will be by the presence of two nucleotides at the relevant position in the DNA sequence. Sequence of the DNA from a subject homozygous for the normal allele or homozygous for the mutation will yield only the presence of the appropriate nucleotide at the relevant position of the DNA sequence.

To provide a suitable template for sequencing, a region of the genomic DNA isolated from the subject may be amplified using appropriately designed primers. Sequencing reactions with an appropriate primer and the analysis of the DNA sequence may be performed by a suitable method known in the art. In the case of the mutation being the −7351 C to T mutation in the upstream region of the tPA locus, a preferred region for amplification. is the region spanning nucleotides 1840 to 2245 of SEQ ID No. 1.

Alternatively, the presence of a mutation may be determined using sequence specific primers that will only amplify either the wild type allele or the allele with the mutation from the DNA isolated from the subject. If sequence specific primers are used to amplify the DNA, a consensus primer and one of two alternative primers will be used. Each of the alternative primers will have a 3' terminal nucleotide that either corresponds to the wild type sequence (a WT primer) or the polymorphic sequence (a SNP primer). In this case, amplification will only occur from the template having the correct complementary nucleotide.

Other methods to identify mutations involve hybridization of nucleic acid containing the mutation with other nucleic acids (ie a reporter nucleic acid) that allows discrimination between differences in nucleic acid sequences. For example, Southern analysis with an oligonucleotide may be used to detect mutations. Alternatively, methods are known in the art in which the oligonucleotide is attached to a solid substrate, such as chip, and the binding of a nucleic acid containing a mutation detected by binding (or lack thereof) to the oligonucleotide. In these cases, the identification of a mutation in a subject also includes detection of the mutation by hybridisation of nucleic acid isolated or derived from the subject to a reporter nucleic acid.

In the case of the mutation being the −7351 C to T mutation, a preferred region of the tPA locus for amplification with WT and SNP primers is the region spanning nucleotides 1840 to 2245 of SEQ ID No. 1.

Accordingly, in another form the present invention provides an isolated nucleic acid, the polynucleotide consisting of the sequence spanning nucleotides 1840 to 2245 of SEQ ID No. 1.

The sequence of the region spanning nucleotides 1840 to 2245 of SEQ ID No.1 is as follows:

```
5'-ATTGGCGCAA ACTCCTCACA GAGGAAAAAA TGTACAGTTA

GAGTGAAGTG AAAGAACATC TCTATAAAAT ATGCATCACT

TCCTGGCGGG GAGGAGAGAG GAGCTATGGA AAGCTACACC

AAAGCTGTAT TCACTGGACA AAAATGCTTG ACTCAGGAAG

GAGGCCGGAG CGGCGAGTCC TGTGATGCCA TGGCGGGAGG

TGGGTCCCAT GTAAACAGTG GTGTTCCTGT CACCCTGAGC

ACATGCAGTC TCCCGTGGGT AACCAGAACT GATGCAAGAG

CCCCTGCTGT GGAAGTCACC ACGCTCTCCC AGAACGCGCC

TCCCCCCAGG TCTGAGTGAT CTCATTGCCG AGGTGAATAG

GGCTTTGGCC GCTCTCCCAA AGGAGCCCGC CCCAGACACA

GCCAT-3'
```

Preferably, the primers used to amplify the region of the tPA locus having the normal −7351 sequence are SEQ ID No. 2 (5'-ATTGGCGCAAACTCCTCACA-3') and SEQ ID No. 3 (5'-ATGGCTGTGTCTGGGGCG-3'), and the primers used to amplify the region of the tPA locus having the −7351 C to T polymorphic sequence are SEQ ID No. 2 (5'-ATTGGCGCAAACTCCTCACA-3') and SEQ ID No. 4 (5'-ATGGCTGTGTCTGGGGCA-3'). Suitable reaction conditions to amplify the tPA locus with these primers include amplification using a PTC-200 Peltier Thermal Cycler (MJ Research) with the following PCR cycling parameters: 5 cycles of 96° C. for 25 seconds, 70° C. for 45 seconds, and 72° C. for 45 seconds; 21 cycles of 96° C. for 25 seconds, 65° C. for 50 seconds, and 72° C. for 45 seconds; 4 cycles of 96° C. for 25 seconds, 55° C. for 60 seconds, and 72° C. for 125 seconds.

The amplification products may be detected by a suitable method known in the art. For example, the amplification products may be run on an agarose gel and stained with ethidium bromide for visualization.

Preferably, the identification of the mutation includes amplification of a region containing the mutation from nucleic acid isolated or derived from the subject.

This form of the present invention is also useful for identifying subjects in need of medical intervention to prevent and/or treat ischemic stroke.

Accordingly, in another form the present invention also provides a method of identifying a subject suitable for intervention to prevent and/or treat ischemic stroke, the method including the step of identifying a mutation in the subject that reduces the release rate of tissue plasminogen activator.

In addition, in a preferred form the present invention also provides a method of identifying a subject suitable for intervention to prevent and/or treat ischemic stroke, the method including the step of identifying in the subject the presence of a cytosine to thymine mutation at position −7351 in both alleles of the tissue plasminogen activator locus.

The present invention also provides a method of identifying a subject predisposed to ischemic stroke, the method include the step of identifying a reduced rate of release of tissue plasminogen activator in the subject.

The ischemic stroke is any thrombotic or embolic stoke that may occur in the subject, including a cardioembolic or atherothrombotic ischemic stroke. Preferably, the ischemic stroke is an atherothrombotic ischemic stroke.

Preferably, the ischemic stroke is a small vessel stroke (ie a lacunar stroke). Accordingly, in a preferred form, the present invention provides a method of identifying a subject predisposed to lacunar stroke, the method include the step of identifying a reduced rate of release of tissue plasminogen activator in the subject.

The subject is any human subject of either gender for which the predisposition to ischemic stroke is to be determined. Preferably, the subject is a human of Caucasian origin.

Preferably, the subject has a mutation in the tPA locus that reduces the release rate of tPA in the subject. More preferably, the subject has a mutation in an upstream region of the tPA locus that reduces the release rate of tPA in the subject. More preferably, the subject has a mutation in an enhancer element in the tPA locus that reduces the release rate of tPA in the subject. Most preferably, the subject has a mutation in a cytosine to thymine at position −7351 of the upstream region of the tPA locus.

The −7351 cytosine to thymine mutation may be present in one or both alleles of the tPA locus. Most preferably, the mutation is present in both alleles of the tPA locus.

The identification of a reduced rate of release of tPA in the subject may by a suitable method known in the art. For example, the rate of release of tPA in a subject may be determined directly, by determination of forearm release rates. A suitable method for determining the rate of release of tPA in vivo is as described in Jern et al. (1999) *Arterioscler. Thromb. Vasc. Biol.* 19(2): 454-459.

This form of the present invention is also useful for identifying subjects in need of medical intervention to prevent and/or treat ischemic stroke.

Accordingly, in another form the present invention also provides a method of identifying a subject suitable for intervention to prevent and/or treat ischemic stroke, the method including the step of identifying a reduced release rate of tissue plasminogen activator in the subject.

The present invention also provides a method of identifying a subject predisposed to small vessel occlusion, the method including the step of identifying a mutation in the subject that reduces the release rate of tissue plasminogen activator.

The subject is any human subject of either gender for which the predisposition to small vessel occlusion is to be determined. Preferably, the subject is a human of Caucasian origin.

The small vessel occlusion in the various forms present invention is any thrombotic or embolic occlusion that may occur in a small vessel in a subject, including small vessel occlusion manifesting clinically as a lacunar stroke, dementia, ischemic heart disease (including ischemic cardiomyopathy), peripheral vascular disease, disseminated intravascular coagulation, small vessel vasculitis, ischemic neuropathy, ischemic retinopathy, ischemic gastropathy (including small and large bowel ischemia), diffuse pulmonary embolism and vascular impotence.

Preferably, the small vessel occlusion occurs in the brain, including a small vessel occlusion manifesting clinically as a lacunar stroke.

The mutation in the subject is any mutation in any gene or extragenic region that reduces the release rate of tPA from an endothelial cell. For example, the mutation may be a mutation in the tPA locus, such as a mutation in a region upstream of the tPA coding region, a mutation in an enhancer element, a mutation in an exon of the tPA gene, a mutation in an intron that affects splicing, or a mutation in the 3' region of the tPA locus that affects translation or mRNA stability.

The mutation may be present in one or both alleles of the particular gene. Most preferably, the mutation is present in both alleles of the particular gene.

As discussed previously, the identification of a mutation in the subject that reduces the release rate of tPA may be determined by a suitable method known in the art.

DNA may be isolated from the subject by a suitable method known in the art. A suitable method for isolating genomic DNA from a subject is from whole venous blood as described in Miller et al. (1988) *Nucleic Acids Research* 16(3):1215.

The ability of a mutation to reduce the release rate of tissue plasminogen activator may be determined by a suitable method known in the art. For example, the ability of specific mutation to reduce the release rate of tPA from endothelial cells may be determined by culturing endothelial cells in vitro carrying the mutation and determining the rate of release of tPA from the endothelial cells, by washing the cells with fresh medium and determining the extent of rate of change of tPA released into the medium over time, as compared to wild type endothelial cells. An enzyme-linked immunosorbent assay (ELISA) may be employed for the quantitative determination of total t-PA antigen (eg TintElize® t-PA, Biopool AB). Such assays are based on the double-antibody principle. Free t-PA and t-PA in complex with inhibitors are detected with equal efficiency.

To induce release of tPA from the endothelial cells, agents known in the art that induce release of tPA may be utilised, such as thrombin or calcium ionophore. A suitable method for inducing the release of tPA from endothelial cells in vitro is as described in Rosnoblet et al. (1999) *Arterioscler Thromb Vasc Biol.* 19(7):1 796-803.

Preferably, the mutation in the subject is a mutation in the tPA locus. More preferably, the mutation is in an upstream region of the tPA locus. More preferably, the mutation is in an enhancer element in the tPA locus. Most preferably, the mutation is a cytosine to thymine mutation at position −7351 of the upstream region of the tPA locus.

The −7351 cytosine to thymine mutation may be present in one or both alleles of the tPA locus. Most preferably, the mutation is present in both alleles of the tPA locus. Accordingly, in a preferred form, the present invention provides a method of identifying a subject predisposed to small vessel occlusion, the method including the step of identifying in the subject the presence of a cytosine to thymine mutation at position −7351 in both alleles of the tissue plasminogen activator locus.

As discusses previously, the identification of a mutation in the subject that reduces the release rate of tPA may be determined by a suitable method known in the art.

DNA may be isolated from the subject by a suitable method known in the art. A suitable method for isolating genomic DNA from a subject is from whole venous blood as described in Miller et al. (1988) *Nucleic Acids Research* 16(3):1215.

As discussed previously, various methods may be used to identify a mutation.

DNA sequencing (either manual sequencing or automated fluorescent sequencing) can be used to detect a mutation. Another approach for identifying mutations is the single-stranded conformation polymorphism assay (SSCA) (as described in Orita et al. (1989) *Genomics* 5(4): 874-879. This method does not detect all sequence changes, especially if the DNA fragment size is greater than 200 bp, but can be optimized to detect most DNA sequence variation. Fragments which have shifted mobility on SSCA gels are then sequenced to determine the exact nature of the DNA sequence variation.

Another approach is based on the detection of mismatches between two complementary DNA strands, including clamped denaturing gel electrophoresis (as described in Sheffield et al. (1991) *Am. J. Hum. Genet.* 49:699-706), heteroduplex analysis (as described in White et al. (1992) *Genomics* 12:301-303) and chemical mismatch cleavage (as described in Grompe et al. (1989) *Proc. Natl. Acad. Sci. USA* 86:5855-5892). Once a specific mutation is identified, an allele specific detection approach such as allele specific oligonucleotide hybridization can be utilized.

If DNA sequence analysis is used to identify a mutation, the presence of a mutation in one allele (ie the subject is heterozygous for the mutation) will be by the presence of two nucleotides at the relevant position in the DNA sequence. Sequence of the DNA from a subject homozygous for the normal allele or homozygous for the mutation will yield only the presence of the appropriate nucleotide at the relevant position of the DNA sequence.

To provide a suitable template for sequencing, a region of the genomic DNA isolated from the subject may be amplified using appropriately designed primers. Sequencing reactions with an appropriate primer and the analysis of the DNA sequence may be performed by a suitable method known in the art. In the case of the mutation being the −7351 C to T mutation in the upstream region of the tPA locus, a preferred region for amplification is the region spanning nucleotides 1840 to 2245 of SEQ ID No. 1.

Alternatively, the presence of a mutation may be determined using sequence specific primers that will only amplify either the wild type allele or the allele with the mutation from the DNA isolated from the subject. If sequence specific primers are used to amplify the DNA, a consensus primer and one of two alternative primers will be used. Each of the alternative primers will have a 3' terminal nucleotide that either corresponds to the wild type sequence (a WT primer) or the polymorphic sequence (a SNP primer). In this case, amplification will only occur from the template having the correct complementary nucleotide.

In the case of the mutation being the −7351 C to T mutation, a preferred region of the tPA locus for amplification with WT and SNP primers is the region spanning nucleotides 1840 to 2245 of SEQ ID No. 1.

Preferably, the primers used to amplify the region of the tPA locus having the normal −7351 sequence are SEQ ID No. 2 (5'-ATTGGCGCAAACTCCTCACA-3') and SEQ ID No. 3 (5'-ATGGCTGTGTCTGGGGCG-3'), and the primers used to amplify the region of the tPA locus having the −7351 C to T polymorphic sequence are SEQ ID No. 2 (5'-ATTGGCG-CAAACTCCTCACA-3') and SEQ ID No. 4 (5'-ATGGCT-GTGTCTGGGGCA-3'). Suitable reaction conditions to amplify the tPA locus with these primers include amplification using a PTC-200 Peltier Thermal Cycler (MJ Research) with the following PCR cycling parameters: 5 cycles of 96° C. for 25 seconds, 70° C. for 45 seconds, and 72° C. for 45 seconds; 21 cycles of 96° C. for 25 seconds, 65° C. for 50 seconds, and 72° C. for 45 seconds; 4 cycles of 96° C. for 25 seconds, 55° C. for 60 seconds, and 72° C. for 125 seconds.

The amplification products may be detected by a suitable method known in the art. For example, the amplification products may be run on an agarose gel and stained with ethidium bromide for visualization.

Preferably, the identification of the mutation includes amplification of a region containing the mutation from nucleic acid isolated or derived from the subject.

Preferably, the identification of the mutation also includes detection of the mutation by hybridisation of nucleic acid isolated or derived from the subject to a reporter nucleic acid.

This form of the present invention is also useful for identifying subjects in need of medical intervention to prevent and/or treat a disease or condition associated with small vessel occlusion.

Accordingly, in another form the present invention also provides a method of identifying a subject suitable for intervention to prevent and/or treat a disease or condition associated with small vessel occlusion, the method including the step of identifying a mutation in the subject that reduces the release rate of tissue plasminogen activator.

In addition, in a preferred form the present invention also provides a method of identifying a subject suitable for intervention to prevent and/or treat a disease or condition associated with small vessel occlusion, the method including the step of identifying in the subject the presence of a cytosine to thymine mutation at position −7351 in both alleles of the tissue plasminogen activator locus.

The present invention also provides a method of identifying a subject predisposed to small vessel occlusion, the method including the step of identifying a reduced rate of release of tissue plasminogen activator in the subject.

The subject is any human subject of either gender for which the predisposition to small vessel occlusion is to be determined. Preferably, the subject is a human of Caucasian origin.

The small vessel occlusion is any thrombotic or embolic occlusion that may occur in a small vessel in a subject, including small vessel occlusion manifesting clinically as a lacunar stroke, dementia, ischemic heart disease (including ischemic cardiomyopathy), peripheral vascular disease, disseminated intravascular coagulation, small vessel vasculitis, ischemic neuropathy, ischemic retinopathy, ischemic gastropathy (including small and large bowel ischemia), diffuse pulmonary embolism and vascular impotence.

Preferably, the small vessel occlusion occurs in the brain, including a small vessel occlusion manifesting clinically as a lacunar stroke.

Preferably, the subject has a mutation in the tPA locus that reduces the release rate of tPA in the subject. More preferably, the subject has a mutation in an upstream region of the tPA locus that reduces the release rate of tPA in the subject. More preferably, the subject has a mutation in an enhancer element in the tPA locus that reduces the release rate of tPA in the subject. Most preferably, the subject has a mutation in a cytosine to thymine at position −7351 of the upstream region of the tPA locus.

The −7351 cytosine to thymine mutation may be present in one or both alleles of the tPA locus. Most preferably, the mutation is present in both alleles of the tPA locus.

The identification of a reduced rate of release of tPA in the subject may by a suitable method known in the art. For example, the rate of release of tPA in a subject may be determined directly, by determination of forearm release rates.

A suitable method for determining the rate of release of tPA in vivo is as described in Jem et al. (1999) *Arterioscler. Thromb. Vasc. Biol.* 19(2): 454-459.

This form of the present invention is also useful for identifying subjects in need of medical intervention to prevent and/or treat a disease or condition associated with small vessel occlusion.

Accordingly, in another form the present invention also provides a method of identifying a subject suitable for intervention to prevent and/or treat a disease or condition associated with small vessel occlusion, the method including the step of identifying a reduced release rate of tissue plasminogen activator in the subject.

The present invention also provides a method of identifying a subject predisposed to a disease or condition associated with small vessel occlusion, the method including the step of identifying in the subject the presence of a cytosine to thymine mutation at position −7351 in both alleles of the tissue plasminogen activator locus.

The subject is any human subject of either gender for which the predisposition to developing a disease or condition associated with small vessel occlusion is to be determined. Preferably, the subject is a human of Caucasian origin.

Example of diseases or conditions associated with small vessel occlusion include lacunar stroke, dementia, ischemic heart disease (including ischemic cardiomyopathy), peripheral vascular disease, disseminated intravascular coagulation, small vessel vasculitis, ischemic neuropathy, ischemic retinopathy, ischemic gastropathy (including small and large bowel ischemia), diffuse pulmonary embolism and vascular impotence.

Preferably, the disease or condition associated with small vessel occlusion occurs in the brain, including a lacunar stroke.

The identification in the subject of the presence of a cytosine to thymine mutation at position −7351 in both alleles of the tissue plasminogen activator locus may be by a suitable method known in the art.

DNA may be isolated from the subject by a suitable method known in the art. A suitable method for isolating genomic DNA from a subject is from whole venous blood as described in Miller et al. (1988) *Nucleic Acids Research* 16(3):1215.

To identify the cytosine to thymine mutation at position −7351 both alleles of the tissue plasminogen activator locus, DNA sequencing (either manual sequencing or automated fluorescent sequencing) can be used to detect a mutation.

As discussed previously, various methods may be used to identify the mutation. If DNA sequence analysis is used to identify the mutation, the presence of a mutation in one allele (ie the subject is heterozygous for the mutation) will be by the presence of two nucleotides (C and T) at the relevant position in the DNA sequence. Sequence of the DNA from a subject homozygous for the normal allele or homozygous for the mutation will yield only the presence of the appropriate nucleotide at the relevant position of the DNA sequence.

To provide a suitable template for sequencing the mutation, a suitable region of the genomic DNA isolated from the subject may be amplified using appropriately designed primers. Sequencing reactions with an appropriate primer and the analysis of the DNA sequence may be performed by a suitable method known in the art. A preferred region for amplification is the region spanning nucleotides 1840 to 2245 of SEQ ID No. 1.

Alternatively, the presence of a mutation in both alleles may be determined using sequence specific primers that will only amplify either the wild type allele or the allele with the mutation from the DNA isolated from the subject. Once again, a preferred region of the tPA locus for amplification with WT and SNP primers is the region spanning nucleotides 1840 to 2245 of SEQ ID No. 1.

Preferably, the primers used to amplify the region of the tPA locus having the normal −7351 sequence are SEQ ID No. 2 (5'-ATTGGCGCAAACTCCTCACA-3') and SEQ ID No. 3 (5'-ATGGCTGTGTCTGGGGCG-3'), and the primers used to amplify the region of the tPA locus having the −7351 C to T polymorphic sequence are SEQ ID No. 2 (5'-ATTGGCGCAAACTCCTCACA-3') and SEQ ID No. 4 (5'-ATGGCTGTGTCTGGGGCA-3'). Suitable reaction conditions to amplify the tPA locus with these primers include amplification using a PTC-200 Peltier Thermal Cycler (MJ Research) with the following PCR cycling parameters: 5 cycles of 96° C. for 25 seconds, 70° C. for 45 seconds, and 72° C. for 45 seconds; 21 cycles of 96° C. for 25 seconds, 65° C. for 50 seconds, and 72° C. for 45 seconds; 4 cycles of 96° C. for 25 seconds, 55° C. for 60 seconds, and 72° C. for 125 seconds.

The amplification products may be detected by a suitable method known in the art. For example, the amplification products may be run on an agarose gel and stained with ethidium bromide for visualization.

Preferably, the identification of the mutation includes amplification of a region containing the mutation from nucleic acid isolated or derived from the subject.

Preferably, the identification of the mutation also includes detection of the mutation by hybridisation of nucleic acid isolated or derived from the subject to a reporter nucleic acid.

This form of the present invention is also useful for identifying subjects in need of medical intervention to prevent and/or treat a disease or condition associated with small vessel occlusion.

Accordingly, in another form the present invention also provides a method of identifying a subject suitable for intervention to prevent and/or treat a disease or condition associated with small vessel occlusion, the method including the step of identifying in the subject the presence of a cytosine to thymine mutation at position −7351 in both alleles of the tissue plasminogen activator locus.

The present invention also provides a method of determining the risk of ischemic stroke in a subject, the method including the step of determining the presence in the subject of a cytosine to thymine mutation at position −7351 in one or both of the alleles of the tissue plasminogen activator locus.

The risk of ischemic stroke in a subject is the probability that a subject with a mutation in the tPA locus may suffer an ischemic stroke as compared to the probability that a subject in the general population may suffer an ischemic stroke, under circumstances where other risk factors (eg atrial fibrillation, history of smoking) for having an ischemic stroke between the subjects are the same.

In this regard, the presence of a cytosine to thymine mutation at position −7351 in one or both alleles of the tPA locus (ie an individual heterozygous for the polymorphism) indicates an elevated risk that the subject may suffer an ischemic stroke as compared to a subject in the general population, under circumstances where other risk factors (eg atrial fibrillation, history of smoking) for having an ischemic stroke or a small vessel occlusion between the subjects are the same. The presence of a mutation in both alleles indicates a further elevated risk over the presence of a mutation in one allele.

For example, the presence in the subject of a cytosine to thymine mutation at position −7351 in one allele of the tissue plasminogen activator locus indicates an increased risk of ischemic stroke in the subject, as compared to the risk of ischemic stroke for a subject not having the mutation in either allele of the tissue plasminogen locus.

Alternatively, the presence in the subject of a cytosine to thymine mutation at position −7351 in one allele of the tissue plasminogen activator locus indicates an increased risk of ischemic stroke in the subject, as compared to the risk of ischemic stroke for a subject in the general population, or an increased risk of ischemic stroke in the subject, as compared to the risk of ischemic stroke for another subject with similar other risk factors for having an ischemic stroke.

In addition, the presence in the subject of a cytosine to thymine mutation at position −7351 in both alleles of the tissue plasminogen activator locus indicates an increased risk of ischemic stroke in the subject, as compared to the risk of ischemic stroke for a subject not having the mutation in one or both alleles of the tissue plasminogen locus.

Alternatively, the presence in the subject of a cytosine to thymine mutation at position −7351 in both alleles of the tissue plasminogen activator locus indicates an increased risk of ischemic stroke in the subject, as compared to the risk of ischemic stroke for a subject in the general population, or indicates an increased risk of ischemic stroke in the subject, as compared to the risk of ischemic stroke for a subject with similar other risk factors for having an ischemic stroke.

The subject is any human subject of either gender for which the risk of suffering an ischemic stroke is to be determined. Preferably, the subject is a human of Caucasian origin.

The ischemic stroke is any thrombotic or embolic stoke that may occur in the subject, including a cardioembolic or atherothrombotic ischemic stroke. Preferably, the ischemic stroke is an atherothrombotic ischemic stroke.

Preferably, the ischemic stroke is a small vessel stroke (ie a lacunar stroke). Accordingly, in a preferred form, the present invention provides a method of determining the risk of lacunar stroke in a subject, the method including the step of determining the presence in the subject of a cytosine to thymine mutation at position −7351 in one or both of the alleles of the tissue plasminogen activator locus.

As discussed previously, determination of the presence in the subject of a cytosine to thymine polymorphism at position −7351 in one or both of the alleles of the tissue plasminogen activator locus may be by a suitable method known in the art.

DNA may be isolated from the subject by a suitable method known in the art. A suitable method for isolating genomic DNA from a subject is from whole venous blood as described in Miller et al. (1988) *Nucleic Acids Research* 16(3):1215.

As discussed previously, various methods can be use to determine the presence of the cytosine to thymine mutation at position −7351 in one or both alleles of the tissue plasminogen activator locus, such as DNA sequencing (either manual sequencing or automated fluorescent sequencing).

If DNA sequence analysis is used to identify the mutation, the presence of a mutation in one allele (ie the subject is heterozygous for the mutation) will be by the presence of two nucleotides (C and T) at the relevant position in the DNA sequence. Sequence of the DNA from a subject homozygous for the normal allele or homozygous for the mutation will yield only the presence of the appropriate nucleotide at the relevant position of the DNA sequence.

To provide a suitable template for sequencing the mutation, a suitable region of the genomic DNA isolated from the subject may be amplified using appropriately designed primers. Sequencing reactions with an appropriate primer and the analysis of the DNA sequence may be performed by a suitable method known in the art. A preferred region for amplification is the region spanning nucleotides 1840 to 2245 of SEQ ID No. 1.

Alternatively, the presence of a mutation may be determined using sequence specific primers that will only amplify either the wild type allele or the allele with the mutation from the DNA isolated from the subject. Once again, a preferred region of the tPA locus for amplification with WT and SNP primers is the region spanning nucleotides 1840 to 2245 of SEQ ID No. 1.

Preferably, the primers used to amplify the region of the tPA locus having the normal −7351 sequence are SEQ ID No. 2 (5'-ATTGGCGCAAACTCCTCACA-3') and SEQ ID No. 3 (5'-ATGGCTGTGTCTGGGGCG-3'), and the primers used to amplify the region of the tPA locus having the −7351 C to T polymorphic sequence are SEQ ID No. 2 (5'-ATTGGCG-CAAACTCCTCACA-3') and SEQ ID No. 4 (5'-ATGGCT-GTGTCTGGGGCA-3'). Suitable reaction conditions to amplify the tPA locus with these primers include amplification using a PTC-200 Peltier Thermal Cycler (MJ Research) with the following PCR cycling parameters: 5 cycles of 96° C. for 25 seconds, 70° C. for 45 seconds, and 72° C. for 45 seconds; 21 cycles of 96° C. for 25 seconds, 65° C. for 50 seconds, and 72° C. for 45 seconds; 4 cycles of 96° C. for 25 seconds, 55° C. for 60 seconds, and 72° C. for 125 seconds.

The amplification products may be detected by a suitable method known in the art. For example, the amplification products may be run on an agarose gel and stained with ethidium bromide for visualization.

Preferably, the identification of the mutation includes amplification of a region containing the mutation from nucleic acid isolated or derived from the subject.

Preferably, the identification of the mutation also includes detection of the mutation by hybridisation of nucleic acid isolated or derived from the subject to a reporter nucleic acid.

The present invention also provides a method of determining the risk of small vessel occlusion in a subject, or the risk of developing a disease or condition associated with small vessel occlusion in a subject, the method including the step of determining the presence in the subject of a cytosine to thymine mutation at position −7351 in one or both of the alleles of the tissue plasminogen activator locus.

The risk of small vessel occlusion in a subject is the probability that a subject with a mutation in the tPA locus may suffer small vessel occlusion as compared to the probability that a subject in the general population may suffer small vessel occlusion, under circumstances where other risk factors for having a small vessel occlusion between the subjects are the same.

In this regard, the presence of a cytosine to thymine mutation at position −7351 in one or both alleles of the tPA locus (ie an individual heterozygous for the polymorphism) indicates an elevated risk that the subject may suffer an a small vessel occlusion as compared to a subject in the general population, under circumstances where other risk factors for having a small vessel occlusion between the subjects are the same. The presence of a mutation in both alleles indicates a further elevated risk over the presence of a mutation in one allele.

For example, the presence in the subject of a cytosine to thymine mutation at position −7351 in one allele of the tissue plasminogen activator locus indicates an increased risk of small vessel occlusion or developing a disease associated with small vessel occlusion in the subject, as compared to the risk for a subject not having the mutation in either alleles of the tissue plasminogen locus.

Alternatively, the presence in the subject of a cytosine to thymine mutation at position −7351 in one allele of the tissue plasminogen activator locus indicates an increased risk of small vessel occlusion or developing a disease associated with small vessel occlusion in the subject, as compared to the risk for a subject in the general population, or an increased risk of small vessel occlusion or developing a disease associated with small vessel occlusion in the subject ischemic stroke in the subject, as compared to the risk for another subject with similar other risk factors for having a small vessel occlusion.

The presence in the subject of a cytosine to thymine mutation at position −7351 in both alleles of the tissue plasminogen activator locus indicates an increased risk of srhall vessel occlusion or developing a disease associated with small vessel occlusion in the subject, as compared to the risk for a subject not having the mutation in one or both alleles of the tissue plasminogen locus.

Alternatively, the presence in the subject of a cytosine to thymine mutation at position −7351 in both alleles of the tissue plasminogen activator locus indicates an increased risk of small vessel occlusion or developing a disease associated with small vessel occlusion in the subject, as compared to the risk for a subject in the general population, or an increased risk of small vessel occlusion or developing a disease associated with small vessel occlusion in the subject, as compared to the risk for another subject with similar other risk factors for having a small vessel occlusion.

The subject is any human subject of either gender for which the risk of suffering a small vessel occlusion is to be determined. Preferably, the subject is a human of Caucasian origin.

The small vessel occlusion is any thrombotic or embolic occlusion that may occur in a small vessel in a subject, including small vessel occlusion manifesting clinically as lacunar stroke, dementia, ischemic heart disease (including ischemic cardiomyopathy), peripheral vascular disease, disseminated intravascular coagulation, small vessel vasculitis, ischemic neuropathy, ischemic retinopathy, ischemic gastropathy (including small and large bowel ischemia), diffuse pulmonary embolism and vascular impotence.

Preferably, the small vessel occlusion occurs in the brain, including a small vessel occlusion manifesting clinically as a lacunar stroke.

As discussed previously, determination of the presence in the subject of a cytosine to thymine polymorphism at position −7351 in one or both of the alleles. of the tissue plasminogen activator locus may be by a suitable method known in the art.

DNA may be isolated from the subject by a suitable method known in the art. A suitable method for isolating genomic DNA from a subject is from whole venous blood as described in Miller et al. (1988) *Nucleic Acids Research* 16(3):1215.

To determine the presence of the cytosine to thymine mutation at position −7351 in one or both alleles of the tissue plasminogen activator locus, DNA sequencing (either manual sequencing or automated fluorescent sequencing) can be used to detect a mutation.

If DNA sequence analysis is used to identify the mutation, the presence of a mutation in one allele (ie the subject is heterozygous for the mutation) will be by the presence of two nucleotides (C and T) at the relevant position in the DNA sequence. Sequence of the DNA from a subject homozygous for the normal allele or homozygous for the mutation will yield only the presence of the appropriate nucleotide at the relevant position of the DNA sequence.

To provide a suitable template for sequencing the mutation, a suitable region of the genomic DNA isolated from the subject may be amplified using appropriately designed primers. Sequencing reactions with an appropriate primer and the analysis of the DNA sequence may be performed by a suitable method known in the art. A preferred region for amplification is the region spanning nucleotides 1840 to 2245 of SEQ ID No. 1.

Alternatively, the presence of a mutation may be determined using sequence specific primers that will only amplify either the wild type allele or the allele with the mutation from the DNA isolated from the subject. Once again, a preferred region of the tPA locus for amplification with WT and SNP primers is the region spanning nucleotides 1840 to 2245 of SEQ ID No. 1.

Preferably, the primers used to amplify the region of the tPA locus having the normal −7351 sequence are SEQ ID No. 2 (5'-ATTGGCGCAAACTCCTCACA-3') and SEQ ID No. 3 (5'-ATGGCTGTGTCTGGGGCG-3'), and the primers used to amplify the region of the tPA locus having the −7351 C to T polymorphic sequence are SEQ ID No. 2 (5'-ATTGGCG-CAAACTCCTCACA-3') and SEQ ID No. 4 (5'-ATGGCT-GTGTCTGGGGCA-3'). Suitable reaction conditions to amplify the tPA locus with these primers include amplification using a PTC-200 Peltier Thermal Cycler (MJ Research) with the following PCR cycling parameters: 5 cycles of 96° C. for 25 seconds, 70° C. for 45 seconds, and 72° C. for 45 seconds; 21 cycles of 96° C. for 25 seconds, 65° C. for 50 seconds, and 72° C. for 45 seconds; 4 cycles of 96° C. for 25 seconds, 55° C. for 60 seconds, and 72° C. for 125 seconds.

The amplification products may be detected by a suitable method known in the art. For example, the amplification products may be run on an agarose gel and stained with ethidium bromide for visualization.

Preferably, the identification of the mutation includes amplification of a region containing the mutation from nucleic acid isolated or derived from the subject.

Preferably, the identification of the mutation also includes detection of the mutation by hybridisation of nucleic acid isolated or derived from the subject to a reporter nucleic acid.

The present invention also provides an isolated nucleic acid consisting of the sequence according to SEQ. ID No. 3 or RNA equivalent thereof, or an isolated nucleic acid with one or more base substitutions in the sequence according to SEQ ID No. 3, wherein the nucleic acid hybridises with the complement of SEQ ID No. 3 under stringent hybridisation conditions and the stringent hybridisation conditions include hybridisation in 6× SSC at 42° C. and washing in 2× SSC at 20° C.

This form of the present invention contemplates an isolated nucleic acid consisting of the sequence according to SEQ ID No. 3 (5'-ATGGCTGTGTCTGGGGCG-3'), or a RNA equivalent thereof, or an isolated nucleic acid with one or more base substitutions of this sequence which hybridises with the complement of SEQ ID No. 3 under stringent hybridisation conditions, wherein the stringent reaction conditions include hybridisation in 6× SSC at 42° C. and washing in 2× SSC at 20° C.

The nucleic acid may be synthesized by a standard method known in the art. For example, phosphorothioate oligonucleotides may be synthesized by the method as described in Stein et al. (1988) *Nucl. Acids Res.* 16: 3209.

Stringent hybridisation conditions are conditions that allow complementary nucleic acids to bind to each other within a range from at or near the Tm (Tm is the melting temperature) to about 20° C. below Tm.

Factors such as the length of the complementary regions, type and composition of the nucleic acids (DNA, RNA, base composition), and the concentration of the salts and other components (e.g. the presence or absence of formamide, dextran sulfate and/or polyethylene glycol) must all be considered, essentially as described in in Current Protocols in Molecular Biology, John Wiley & Sons, N.Y. (1989).

For example, conditions that allowing the nucleic acid to hybridise with the complement of SEQ ID No. 3 under stringent conditions are as follows: prehybridization may be performed in a prehybridization solution (eg 6× SSC (1×=150 mM NaCl, 15 mM sodium citrate, pH 7.0), 5× Denhardt's reagent (1 g/l each of Ficoll, Polyvinyl-pyrrolidone, Bovine Serum Albumin), 1.0% SDS, 100 ug/ml denatured, fragmented salmon sperm DNA) for 2 to 12 hours. Hybridizition of the probe with the target (ie filter) may then be performed under conditions such as 6× SSC, 1.0% SDS, 100 ug/ml denatured, fragmented salmon sperm DNA, at 42° C. overnight. The filter may then be washed with 2× SSC and 0.5% SDS at room temperature for 15 min at 20° C.

The present invention also provides an isolated nucleic acid consisting of the sequence according to SEQ. ID No. 4 or RNA equivalent thereof, or an isolated nucleic acid with one or more base substitutions in the sequence according to SEQ ID No. 4, wherein the nucleic acid hybridises with the complement of SEQ ID No. 4 under stringent hybridisation conditions and the stringent hybridisation conditions include hybridisation in 6× SSC at 42° C. and washing in 2× SSC at 20° C.

This form of the present invention contemplates an isolated nucleic acid consisting of the sequence according to SEQ ID No. 4 (5'-ATGGCTGTGTCTGGGGCA-3') or a RNA equivalent thereof, or an isolated nucleic acid with one or more base substitutions of this sequence which hybridises with the complement of SEQ ID No. 4 under stringent hybridisation conditions, wherein the stringent reaction conditions include hybridisation in 6× SSC at 42° C. and washing in 2× SSC at 20° C.

The nucleic acid may be synthesized by a standard method known in the art. For example, phosphorothioate oligonucleotides may be synthesized by the method as described in Stein et al. (1988) Nucl. Acids Res. 16: 3209.

Stringent hybridisation conditions are conditions that allow complementary nucleic acids to bind to each other within a range from at or near the Tm (Tm is the melting temperature) to about 20° C. below Tm.

Factors such as the length of the complementary regions, type and composition of the nucleic acids (DNA, RNA, base composition), and the concentration of the salts and other components (e.g. the presence or absence of formamide, dextran sulfate and/or polyethylene glycol) must all be considered, essentially as described in in Current Protocols in Molecular Biology, John Wiley & Sons, N.Y. (1989).

For example, conditions that allowing the nucleic acid to hybridise with the complement of SEQ ID No. 4 under stringent conditions are as follows: prehybridization may be performed in a prehybridization solution (eg 6× SSC (1×=150 mM NaCl, 15 mM sodium citrate, pH 7.0), 5×Denhardt's reagent (1 g/l each of Ficoll, Polyvinyl-pyrrolidone, Bovine Serum Albumin), 1.0% SDS, 10 ug/ml denatured, fragmented salmon sperm DNA) for 2 to 12 hours. Hybridizition of the probe with the target (ie filter) may then be performed under conditions such as 6× SSC, –1.0% SDS, 100 ug/ml denatured, fragmented salmon sperm DNA, at 42° C. overnight. The filter may then be washed with 2× SSC and 0.5% SDS at room temperature for 15 min at 20° C.

The present invention also provides an isolated nucleic acid with one or more base substitutions in the sequence according to SEQ ID No. 3, wherein the nucleic acid has at least 80% homology to SEQ. ID No. 3 or RNA equivalent thereof.

This form of the present invention contemplates an isolated nucleic acid with one or more substitutions in the sequence of SEQ ID No. 3, the nucleic acid having at least 80% homology to SEQ ID No. 3 or RNA equivalent thereof.

Various algorithms exist for determining the degree of homology between any two nucleic acid sequences. For example, the BLAST algorithm can be used for determining the extent of sequence homology between two sequences. BLAST identifies local alignments between two sequences and predicts the probability of the local alignment occurring by chance. The BLAST algorithm is as described in Altschul etal., 1990, J. Mol. Biol. 215:403-410.

Preferably, the nucleic has at least 90% homology to SEQ. ID No. 3 or RNA equivalent thereof. Most preferably, the nucleic has at least 95% homology to SEQ. ID No. 3 or RNA equivalent thereof.

The nucleic acid may be synthesized by a standard method known in the art. For example, phosphorothioate oligonucleotides may be synthesized by the method as described in Stein et al. (1988) Nucl. Acids Res. 16: 3209.

The present invention also provides an isolated nucleic acid with one or more base substitutions in the sequence according to SEQ ID No. 4, wherein the nucleic acid has at least 80% homology to SEQ. ID No. 4 or RNA equivalent thereof.

This form of the present invention contemplates an isolated nucleic acid with one or more substitutions in the sequence of SEQ ID No. 4, the nucleic acid having at least 80% homology to SEQ ID No. 4 or RNA equivalent thereof.

Once again, various algorithms exist for determining the degree of homology between any two nucleic acid sequences. For example, the BLAST algorithm can be used for determining the extent of sequence homology between two sequences. BLAST identifies local alignments between two sequences and predicts the probability of the local alignment occurring by chance. The BLAST algorithm is as described in Altschul et al., 1990, J. Mol. Biol. 215:403-410.

Preferably, the nucleic has at least 90% homology to SEQ. ID No. 4 or RNA equivalent thereof. Most preferably, the nucleic has at least 95% homology to SEQ. ID No. 4 or RNA equivalent thereof.

The nucleic acid may be synthesized by a standard method known in the art. For example, phosphorothioate oligonucleotides may be synthesized by the method as described in Stein et al. (1988) Nucl. Acids Res. 16: 3209.

The present invention also provides a method of identifying an agent capable of increasing the release rate of tissue plasminogen activator from a cell, the method including the steps of:

(a) exposing an agent to a cell including a mutation that decreases the release rate of tissue plasminogen activator from the cell;
(b) determining the release rate of tissue plasminogen activator from the cell so exposed to the agent; and
(c) identifying the agent as an agent capable of increasing the release rate of tissue plasminogen activator from the cell.

This form of the present invention is directed to the identification of agents that are capable of increasing the release rate of tissue plasminogen activator from a cell. Agents so identified are candidate compounds for administering to a subject to reduce the likelihood of the subject suffering an ischemic stroke or a small vessel occlusion, and in particular a lacunar stroke.

The agent is any agent for which the ability to increase the release rate of tissue plasminogen activator from the cell is to be determined.

The term "exposing" is be understood to include within its scope the external administration of the agent to a cell or the intracellular expression of the agent in the cell. Accordingly, the exposing of an agent to a cell may be by way of contacting the cell with the agent, or for example, by way of transforming the cell with a recombinant nucleic acid capable of directing the expression of the agent in the cell.

The cell is any cell having a mutation that decreases the release rate of tissue plasminogen activator (as compared to a similar cell not having the mutation).

Preferably the cell is an endothelial cell. Most preferably, the endothelial cell is a human endothelial cell. An example of a suitable endothelial cell is a human umbilical vein endothelial cell (HUVEC).

The mutation in the cell is any mutation that reduces the release rate of tPA from the cell. For example, the mutation may be in a gene or region not associated with the tPA locus, or be a mutation in the tPA locus, such as a mutation in a region upstream of the tPA coding region that affects transcription of the tPA gene, a mutation in an exon of the tPA gene, a mutation in an intron that affects splicing, or a mutation in the 3' region of the tPA that affects translation or mRNA stability.

The mutation may be present in one or both alleles of the particular gene.

Preferably, the mutation is a mutation in the tPA locus that reduces the release rate of tPA from an endothelial cell.

The ability of a mutation to reduce the release rate of tissue plasminogen activator may be confirmed by a suitable method known in the art. For example, the ability of specific mutation in the tPA locus to reduce the release rate of tPA from endothelial cells may be determined by culturing endothelial cells in vitro carrying the mutation and determining the rate of release of tPA from the endothelial cells, by washing the cells with fresh medium and determining the extent of rate of change of tPA released into the medium over time, as compared to wild type endothelial cells. To induce release of tPA from the endothelial cells, agents known in the art that induce secretion of tPA may be utilised, such as thrombin or calcium ionophore. A suitable method for inducing the release of tPA from endothelial cells in vitro is as described in Rosnoblet et al. (1999) *Arterioscler Thromb Vasc Biol.* 19(7): 1796-803.

An enzyme-linked immunosorbent assay (ELISA) may be employed for the quantitative determination of total t-PA antigen (eg TintElize® t-PA, Biopool AB). Such assays are based on the double-antibody principle. Free t-PA and t-PA in complex with inhibitors are detected with equal efficiency.

Preferably, the mutation in the cell is a mutation in an upstream region of the tPA gene. More preferably, the mutation is a mutation in an enhancer element in the tPA gene. Most preferably, the mutation is a cytosine to thymine mutation at position −7351 of the upstream region of the tPA locus.

The −7351 cytosine to thymine mutation may be present in one or both alleles of the tPA locus.

Accordingly, in a preferred form, the present invention also provides a method of identifying an agent capable of increasing the release rate of tissue plasminogen activator from a cell, the method including the steps of:
  (a) exposing an agent to a cell including a cytosine to thymine polymorphism at position −7351 in one or both alleles of the tissue plasminogen activator locus;
  (b) determining the release rate of tissue plasminogen activator from the cell so exposed to the agent; and
  (c) identifying the agent as an agent capable of increasing the release rate of tissue plasminogen activator from the cell.

Most preferably, the −7351 cytosine to thymine mutation is present in both alleles of the tPA locus.

As will be appreciated, the ability of an agent to increase the release rate of tissue plasminogen activator from a cell will depend on the concentration of the agent exposed to the cell. Accordingly, the agent will be exposed to the cell at a suitable concentration for testing the ability of the agent at that concentration to increase the release rate of tissue plasminogen activator from the cell.

A known agent that increases rate of release of tPA from endothelial cells is monosodium [2-(6-hydroxynaphthalen-2-yl)-6-methyl-pyrimidin4-yloxy]acetate dihydrate (JTV-926) (Ueshima et al. (2002) "Function of tissue-type plasminogen activator releaser on vascular endothelial cells in thrombolysis in vivo" *Thrombosis Haemostasis* 87: 1069-74).

The determination of the release rate of tissue plasminogen activator from a cell may be performed by a suitable method known in the art. For example, the ability of an agent to alter the release rate of tPA from endothelial cells may be determined by culturing endothelial cells in vitro and determining the rate of release of tPA from the endothelial cells in the presence and absence of the agent. To determine release rates, the cells may be washed with fresh medium and the extent of rate of change of tPA released into the medium over time determined. To induce release of tPA from the endothelial cells, compounds known in the art that induce secretion of tPA may be utilised, such as thrombin or calcium ionophore. A suitable method for inducing the release of tPA from endothelial cells in vitro is as described in Rosnoblet et al. (1999) *Arterioscler Thromb Vasc BioL* 19(7):1796-803.

An enzyme-linked immunosorbent assay (ELISA) may be employed for the quantitative determination of total t-PA antigen (eg TintElize® t-PA, Biopool AB). Such assays are based on the double-antibody principle. Free t-PA and t-PA in complex with inhibitors are detected with equal efficiency.

Agents that increase the release rate of tPA may be so identified by comparison of the effect of the agents on tPA release rates, as compared to release rates in the absence of an agent, and as compared to known agents that increase the release rate of tPA (eg JTV-926). An agent capable of increasing the release rate of tissue plasminogen activator so identified is a candidate compound for administering to subject to reduce the likelihood of the subject suffering an ischemic stroke (in particular lacunar strokes) or a small vessel occlusion.

The present invention also provides a method of identifying an agent capable of increasing the release rate of tissue plasminogen activator from a cell, the method including the steps of:
  (a) exposing an agent to a cell transformed with all or part of the tissue plasminogen activator locus, wherein the transformed locus includes a cytosine to thymine mutation at position −7351 and the transformed locus regulates expression of a reporter gene;
  (b) determining the level of expression of the reporter gene in the cell so exposed to the agent;
  (c) identifying an agent capable of increasing the expression of the reporter gene; and
  (d) identifying the agent capable of increasing the expression of the reporter gene as an agent capable of increasing the release rate of tissue plasminogen activator from a cell.

This form of the present invention is also directed to the identification of agents that are capable of increasing the release rate of tissue plasminogen activator from a cell. Agents so identified are candidate compounds for administering to subject to reduce the likelihood of the subject suffering an ischemic stroke (in particular lacunar stroke) or a small vessel occlusion.

The cell is any cell transformed with all or part of the tissue plasminogen locus having a cytosine to thymine mutation at position −7351 and regulating the expression of a suitable reporter gene.

Examples of a suitable cell that may be transformed include endothelial cells (eg HUVECs, bovine aortic endothelial cells) and HeLa cells.

Preferably the transformed cell is an endothelial cell. More preferably, the transformed cell is a human endothelial cell. Most preferably, the endothelial cell is a HUVEC.

The DNA coding for all or part of the tPA locus which is to be used to drive the expression of a reporter gene may be derived from an appropriate human genomic clone, the clone produced by a suitable method known in the art.

For example, the tPA locus having the C to T mutation at position −7351 may be cloned from genomic DNA by performing a partial digestion of the DNA with a restriction enzyme (eg Sau 3A1) and shot gun cloning into a lambda or cosmid vector as described in Sambrook, J, Fritsch, E. F. and Maniatis, T. Molecular Cloning: A Laboratory Manual 2nd. ed. Cold Spring Harbor Laboratory Press, New York. (1989). The library may be screened with an appropriate probe (eg a labelled oligonucleotide or a nick translated fragment from the upstream region of the tPA locus) to isolated an appropriate clone, as also described in Sambrook et al. (1998).

Alternatively, all or part of the tPA locus may be generated by PCR amplification from the genomic DNA, using appropriate primers, as described in as described in Dieffenbach, C. W. and G. S. Dveksler (1995) PCR Primer, a Laboratory Manual, Cold Spring Harbor Press, Plainview, N.Y.

In the case where part of the tissue plasminogen locus is used to regulate expression of a reporter gene, the ability of the part of the tPA locus to regulate appropriate expression in endothelial cells will be determined. For example, the ability of the part of the tissue plasminogen locus to induce expression of the reporter gene in response to treatment with thrombin or calcium ionophore can be determined.

The DNA containing the region for cloning may then be fused to an appropriate reporter gene by standard cloning protocols, as described in Sambrook, J, Fritsch, E. F. and Maniatis, T. Molecular Cloning: A Laboratory Manual 2nd. ed. Cold Spring Harbor Laboratory Press, New York. (1989)

Examples of suitable reporter genes include the chloramphenicol acetyltransferase (CAT) gene, green fluorescent protein (and variants thereof), and luciferase.

Transfection of endothelial cells with the reporter gene constructs may be performed by a suitable method known in the art, including the calcium phosphate precipitation method, incorporating a glycerol shock, as described in Sambrook, J, Fritsch, E. F. and Maniatis, T. Molecular Cloning: A Laboratory Manual 2nd. ed. Cold Spring Harbor Laboratory Press, New York. (1989). After exposure, cells may be harvested and relative changes in reporter gene activity quantitated.

To induce expression driven from the tPA locus, an agent known in the art that induce release of tPA may be utilised, such as thrombin or calcium ionophore. A suitable method is as described in Rosnoblet et al. (1999) *Arterioscler Thromb Vasc Biol.* 19(7):1796-803.

Transfection efficiency may also be evaluated by cotransfecting the cells with an appropriate control construct, such as the cytomegalovirus promoter and lac Z gene construct. β-Galactosidase assay may then be performed as described in Sambrook, J, Fritsch, E. F. and Maniatis, T. Molecular Cloning: A Laboratory Manual 2nd. ed. Cold Spring Harbor Laboratory Press, New York. (1989), and may be taken as a direct index of the efficiency of transfection and used to normalize reporter gene activities among various experiments.

An agent that is capable of increasing the expression of the reporter gene may then be tested for its ability to increase the release rate of tPA from a cell. As will be appreciated, the ability of an agent to increase the expression of the reporter gene will depend on the concentration of the agent exposed to the cell. Accordingly, the agent will be exposed to the cell at a suitable concentration for testing the ability of the agent at that concentration to increase the expression of the reporter gene.

The ability of the agent to increase the release rate of tissue plasminogen activator from a cell may then be determined by a suitable method known in the art. For example, the ability of an agent to increase the release rate of tPA from endothelial cells (with or without the C to T mutation at position −7351 in the tPA locus) may be determined by culturing endothelial cells in vitro and determining the rate of release of tPA from the endothelial cells in the presence and absence of the agent.

To determine release rates, the cells may be washed with fresh medium and the extent of rate of change of tPA released into the medium over time determined. To induce release of tPA from the endothelial cells, compounds known in the art that induce secretion of tPA may be utilised, such as thrombin or calcium ionophore. A suitable method for inducing the release of tPA from endothelial cells in vitro is as described in Rosnoblet et al. (1999) *Arterioscler Thromb Vasc Biol.* 19(7): 1796-803.

An enzyme-linked immunosorbent assay (ELISA) may be employed for the quantitative determination of total t-PA antigen (eg TintElize® t-PA, Biopool AB). Such assays are based on the double-antibody principle. Free t-PA and t-PA in complex with inhibitors are detected with equal efficiency.

A known agent that increases rate of release of tPA from endothelial cells is monosodium [2-(6-hydroxynaphthalen-2-yl)-6-methyl-pyrimidin-4-yloxy]acetate dihydrate (JTV-926) (Ueshima et al. (2002) "Function of tissue-type plasminogen activator releaser on vascular endothelial cells in thrombolysis in vivo" *Thrombosis Haemostasis* 87: 1069-74).

The present invention also provides a method of identifying a subject suitable for treatment with an agent that increases the rate of release of tissue plasminogen activator, the method including the step of identifying in the subject. the presence of a cytosine to thymine polymorphism at position −7351 in one or both alleles of the tissue plasminogen locus.

The subject is any human subject of either gender for whom the treatment with an agent that increases the rate of release of tissue plasminogen activator may be beneficial. Preferably, the subject is a human of Caucasian origin.

In this regard, subjects that may benefit from the treatment with an agent that increase the rate of release of tissue plasminogen activator are subjects at increased risk of an ischemic stroke or a small vessel occlusion, and in particular an increased risk of lacunar stroke.

Preferably, the subject suitable for treatment has a cytosine to thymine polymorphism at position −7351 in both alleles of the tissue plasminogen locus.

Accordingly, in a preferred form, the present invention provides a method of identifying a subject suitable for treatment with an agent that increases the rate of release of tissue plasminogen activator, the method including the step of identifying in the subject the presence of a cytosine to thymine polymorphism at position −7351 in both alleles of the tissue plasminogen locus.

An example of an agent that increases the rate of release of tissue plasminogen activator is monosodium [2-(6-hydroxynaphthalen-2-yl)-6-methyl-pyrimidin-4-yloxy]acetate dihydrate (JTV-926) (Ueshima et al. (2002) "Function of tissue-type plasminogen activator releaser on vascular endothelial cells in thrombolysis in vivo" *Thrombosis Haemostasis* 87: 1069-74).

The identification in the subject of the presence of a cytosine to thymine mutation at position −7351 in one or both alleles of the tissue plasminogen activator locus may be by a suitable method known in the art.

DNA may be isolated from the subject by a suitable method known in the art. A suitable method for isolating genomic DNA from a subject is from whole venous blood as described in Miller et al. (1988) *Nucleic Acids Research* 16(3): 1215.

To identify the cytosine to thymine mutation at position −7351 in one or both alleles of the tissue plasminogen activator locus, DNA sequencing (either manual sequencing or automated fluorescent sequencing) can be used to detect a mutation.

If DNA sequence analysis is used to identify the mutation, the presence of a mutation in one allele (ie the subject is heterozygous for the mutation) will be by the presence of two nucleotides (C and T) at the relevant position in the DNA sequence. Sequence of the DNA from a subject homozygous for the normal allele or homozygous for the mutation will yield only the presence of the appropriate nucleotide at the relevant position of the DNA sequence.

To provide a suitable template for sequencing the mutation, a suitable region of the genomic DNA isolated from the subject may be amplified using appropriately designed primers. Sequencing reactions with an appropriate primer and the analysis of the DNA sequence may be performed by a suitable method known in the art. A preferred region for amplification is the region spanning nucleotides 1840 to 2245 of SEQ ID No. 1.

Alternatively, the presence of a mutation may be determined using sequence specific primers that will only amplify either the wild type allele or the allele with the mutation from the DNA isolated from the subject. Once again, a preferred region of the tPA locus for amplification with WT and SNP primers is the region spanning nucleotides 1840 to 2245 of SEQ ID No. 1.

Preferably, the primers used to amplify the region of the tPA locus having the normal −7351 sequence are SEQ ID No. 2 (5'-ATTGGCGCAMCTCCTCACA-3') and SEQ ID No. 3 (5'-ATGGCTGTGTCTGGGGCG-3'), and the primers used to amplify the region of the tPA locus having the −7351 C to T polymorphic sequence are SEQ ID No. 2 (5'-ATTGGCGC-MACTCCTCACA-3') and SEQ ID No. 4 (5'-ATGGCTGT-GTCTGGGGCA-3'). Suitable reaction conditions to amplify the tPA locus with these primers include amplification using a PTC-200 Peltier Thermal Cycler (MJ Research) with the following PCR cycling parameters: 5 cycles of 96° C. for 25 seconds, 70° C. for 45 seconds, and 72° C. for 45 seconds; 21 cycles of 96° C. for 25 seconds, 65° C. for 50 seconds, and 72° C. for 45 seconds; 4 cycles of 96° C. for 25 seconds, 55° C. for 60 seconds, and 72° C. for 125 seconds.

The amplification products may be detected by a suitable method known in the art. For example, the amplification products may be run on an agarose gel and stained with ethidium bromide for visualization.

Preferably, the identification of the mutation includes amplification of a region containing the mutation from nucleic acid isolated or derived from the subject.

Preferably, the identification of the mutation also includes detection of the mutation by hybridisation of nucleic acid isolated or derived from the subject to a reporter nucleic acid.

The present invention also provides a method of treating a disease or condition associated with small vessel occlusion in a subject, the method including the step of administering to the subject an effective amount of an agent that increases the rate of release of tissue plasminogen activator in the subject.

The subject is any human subject susceptible to, or suffering from, a disease or condition associated with small vessel occlusion.

Accordingly, in another form, the present invention also provides a method of treating a subject susceptible to a disease or condition associated with small vessel occlusion, the method including the step of administering to the subject an effective amount of an agent that increases the rate of release of tissue plasminogen activator in the subject.

Example of diseases or conditions associated with small vessel occlusion include lacunar stroke, dementia, ischemic heart disease (including ischemic cardiomyopathy), peripheral vascular disease, disseminated intravascular coagulation, small vessel vasculitis, ischemic neuropathy, ischemic retinopathy, ischemic gastropathy (including small and large bowel ischemia), diffuse pulmonary embolism and vascular impotence.

Preferably, the disease or condition associated with small vessel occlusion occurs in the brain, including a lacunar stroke.

Accordingly, in a preferred form, the present invention also provides a method of treating a lacunar stroke in a subject, the method including the step of administering to the subject an effective amount of an agent that increases the rate of release of tissue plasminogen activator in the subject.

In another preferred form, the present invention provides a method of treating a subject susceptible to lacunar stroke, the method including the step of administering to the subject an effective amount of an agent that increases the rate of release of tissue plasminogen activator in the subject.

The agent is any agent that when administered to a subject has the capacity to increase the rate of release of tPA. An example of an agent that has the capacity to increase the release rate of tPA is monosodium [2-(6-hydroxynaphthalen-2-yl)-6-methyl-pyrimidin-4-yloxy]acetate dihydrate (JTV-926) (Ueshima et al. (2002) "Function of tissue-type plasminogen activator releaser on vascular endothelial cells in thrombolysis in vivo" *Thrombosis Haemostasis* 87: 1069-74).

The effective amount of the agent that increases the release rate of tPA to be administered to a subject is not particularly limited, so long as it is within such an amount and in such a form that generally exhibits a pharmacologically useful or therapeutic effect.

In this regard, an effective amount of the agent that increases the release rate of tPA may be appropriately chosen, depending upon the extent of increase in the rate of release of tPA to be achieved in the subject, the types of diseases or conditions associated with small vessel occlusion to be treated, the age and body weight of the subject, the frequency of administration, and the presence of other active agents.

The administration of the agent that increases the release rate of tPA may be within any time suitable to produce the desired effect of increasing the rate of release of tPA in the subject, and may be administered orally, parenterally or by any other suitable means, and therefore transit time of the drug must be taken into account.

The administration of the agent that increases the release rate of tPA may also include the use of one or more pharmaceutically acceptable additives, including pharmaceutically acceptable salts, amino acids, polypeptides, polymers, solvents, buffers, excipients and bulking agents, taking into consideration the particular physical and chemical characteristics of the agent that increases the release rate of tPA to be administered.

For example, the agent that increases the release rate of tPA can be prepared into a variety of pharmaceutical preparations in the form of, e.g., an aqueous solution, an oily preparation, a fatty emulsion, an emulsion, a gel, etc., and these preparations can be administered as intramuscular or subcutaneous injection or as injection to the organ, or as an embedded preparation or as a transmucosal preparation through nasal cavity, rectum, uterus, vagina, lung, etc. The composition may be administered in the form of oral preparations (for example solid preparations such as tablets, capsules, granules or powders; liquid preparations such as syrup, emulsions or suspensions). Compositions containing the agent that increases the release rate of tPA may also contain a preservative, stabilizer, dispersing agent, pH controller or isotonic agent. Examples of suitable preservatives are glycerin, propylene glycol, phenol or benzyl alcohol. Examples of suitable stabilizers are dextran, gelatin, α-tocopherol acetate or alpha-thioglycerin. Examples of suitable dispersing agents include polyoxyethylene (20), sorbitan mono-oleate (Tween 80), sorbitan sesquioleate (Span 30), polyoxyethylene (160) polyoxypropylene (30) glycol (Pluronic F68) or polyoxyethylene hydrogenated castor oil 60. Examples of suitable pH controllers include hydrochloric acid, sodium hydroxide and the like. Examples of suitable isotonic agents are glucose, D-sorbitol or D-mannitol.

The administration of the agent that increases the release rate of tPA may also be in the form of a composition containing a pharmaceutically acceptable carrier, diluent, excipient, suspending agent, lubricating agent, adjuvant, vehicle, delivery system, emulsifier, disintegrant, absorbent, preservative, surfactant, colorant, flavorant or sweetener, taking into account the physical and chemical properties of the agent that increases the release rate of tPA.

For these purposes, the composition may be administered orally, parenterally, by inhalation spray, adsorption, absorption, topically, rectally, nasally, bucally, vaginally, intraventricularly, via an implanted reservoir in dosage formulations containing conventional non-toxic pharmaceutically-acceptable carriers, or by any other convenient dosage form. The term parenteral as used herein includes subcutaneous, intravenous, intramuscular, intraperitoneal, intrathecal, intraventricular, intrasternal, and intracranial injection or infusion techniques.

When administered parenterally, the composition will normally be in a unit dosage, sterile injectable form (solution, suspension or emulsion) which is preferably isotonic with the blood of the recipient with a pharmaceutically acceptable carrier. Examples of such sterile injectable forms are sterile injectable aqueous or oleaginous suspensions. These suspensions may be formulated according to techniques known in the art using suitable dispersing or wetting agents and suspending agents. The sterile injectable forms may also be sterile injectable solutions or suspensions in non-toxic parenterally-acceptable diluents or solvents, for example, as solutions in 1,3-butanediol. Among the acceptable vehicles and solvents that may be employed are water, saline, Ringer's solution, dextrose solution, isotonic sodium chloride solution, and Hanks' solution. In addition, sterile, fixed oils are conventionally employed as solvents or suspending mediums. For this purpose, any bland fixed oil may be employed including synthetic mono- or di-glycerides, corn, cottonseed, peanut, and sesame oil. Fatty acids such as ethyl oleate, isopropyl myristate, and oleic acid and its glyceride derivatives, including olive oil and castor oil, especially in their polyoxyethylated versions, are useful in the preparation of injectables. These oil solutions or suspensions may also contain long-chain alcohol diluents or dispersants.

The carrier may contain minor amounts of additives, such as substances that enhance solubility, isotonicity, and chemical stability, for example anti-oxidants, buffers and preservatives.

When administered orally, the composition will usually be formulated into unit dosage forms such as tablets, cachets, powder, granules, beads, chewable lozenges, capsules, liquids, aqueous suspensions or solutions, or similar dosage forms, using conventional equipment and techniques known in the art. Such formulations typically include a solid, semi-solid, or liquid carrier. Exemplary carriers include lactose, dextrose, sucrose, sorbitol, mannitol, starches, gum acacia, calcium phosphate, mineral oil, cocoa butter, oil of theobroma, alginates, tragacanth, gelatin, syrup, methyl cellulose, polyoxyethylene sorbitan monolaurate, methyl hydroxybenzoate, propyl hydroxybenzoate, talc, magnesium stearate, and the like.

A tablet may be made by compressing or molding the active ingredient optionally with one or more accessory ingredients. Compressed tablets may be prepared by compressing, in a suitable machine, the active ingredient in a free-flowing form such as a powder or granules, optionally mixed with a binder, lubricant, inert diluent, surface active, or dispersing agent. Molded tablets may be made by molding in a suitable machine, a mixture of the powdered active ingredient and a suitable carrier moistened with an inert liquid diluent.

The administration of the agent that increases the release rate of tPA may also utilize controlled release technology. The agent that increases the release rate of tPA may also be administered as a sustained-release pharmaceutical. To further increase the sustained release effect, the composition may be formulated with additional components such as vegetable oil (for example soybean oil, sesame oil, camellia oil, castor oil, peanut oil, rape seed oil); middle fatty acid triglycerides; fatty acid esters such as ethyl oleate; polysiloxane derivatives; alternatively, water-soluble high molecular weight compounds such as hyaluronic acid or salts thereof (weight average molecular weight: ca. 80,000 to 2,000,000), carboxymethylcellulose sodium (weight average molecular weight: ca. 20,000 to 400,000), hydroxypropylcellulose (viscosity in 2% aqueous solution: 3 to 4,000 cps), atherocollagen (weight average molecular weight: ca. 300,000), polyethylene glycol (weight average molecular weight: ca. 400 to 20,000), polyethylene oxide (weight average molecular weight: ca. 100,000 to 9,000,000), hydroxypropylmethylcellulose (viscosity in 1% aqueous solution: 4 to 100,000 cSt), methylcellulose (viscosity in 2% aqueous solution: 15 to 8,000 cSt), polyvinyl alcohol (viscosity: 2 to 100 cSt), polyvinylpyrrolidone (weight average molecular weight: 25,000 to 1,200,000).

Alternatively, the agent that increases the release rate of tPA may be incorporated into a hydrophobic polymer matrix for controlled release over a period of days. The composition of the invention may then be molded into a solid implant, or externally applied patch, suitable for providing efficacious concentrations of the agent that increases the release rate of tPA over a prolonged period of time without the need for frequent re-dosing. Such controlled release films are well known to the art. Other examples of polymers commonly employed for this purpose that may be used include nondegradable ethylene-vinyl acetate copolymer a degradable lactic acid-glycolic acid copolymers which may be used externally or internally. Certain hydrogels such as poly (hydroxyethylmethacrylate) or poly(vinylalcohol) also may be useful, but for shorter release cycles than the other polymer release systems, such as those mentioned above.

The carrier may also be a solid biodegradable polymer or mixture of biodegradable polymers with appropriate time release characteristics and release kinetics. The composition may then be molded into a solid implant suitable for providing efficacious concentrations of the agent that increases the release rate of tPA over a prolonged period of time without the need for frequent re-dosing. The agent that increases the release rate of tPA can be incorporated into the biodegradable polymer or polymer mixture in any suitable manner known to one of ordinary skill in the art and may form a homogeneous matrix with the biodegradable polymer, or may be encapsulated in some way within the polymer, or may be molded into a solid implant.

DESCRIPTION OF THE PREFERRED EMBODIMENTS

Reference will now be made to experiments that embody the above general principles of the present invention. However, it is to be understood that the following description is not to limit the generality of the above description.

EXAMPLE 1

Isolation of Genomic DNA

Genomic DNA was isolated from six millilitres of whole venous blood as described in Miller, S. A., D. D. Dykes, and H. F. Polesky (1988). "A simple salting out procedure for extracting DNA from human nucleated cells" *Nucleic Acids Research* 16(3): 1215.

EXAMPLE 2

Oligonucleotide Primers

The sequence of the two reverse allele-specific primers is as follows:

```
SNP primer:
5'-ATGGCTGTGTCTGGGGCG-3';      (SEQ ID No. 3)

WT primer:
5'-ATGGCTGTGTCTGGGGCA-3',      (SEQ ID No. 4)

Forward consensus primer:
5'-ATTGGCGCAAACTCCTCACA-3'.    (SEQ ID NO. 2)
```

The relative position of the primers in the DNA sequence is shown in FIG. 1. These primers result in a 405 base pair DNA amplified fragment (spanning nucleotides 1840-2245 of GenBank Accession No. Z48484; SEQ ID No. 1) of the tPA gene The sequence of the two positive control primers coding for a 600bp fragment of the HLA-DRB3 gene is as follows:

```
Forward
(sense) primer:       5'-TGCCAAGTGGAGCACCCAA-3'
(SEQ ID
NO: 5)

Reverse
(anti-sense) primer:  5'-GCATCTTGCTCTGTGCAGAT-3'
(SEQ ID
NO: 6)
```

Forward (sense) primer (SEQ ID NO: 5): 5'-TGCCAAGTGGAGCACCCAA-3'

Reverse (anti-sense) primer (SEQ ID NO: 6): 5'-GCATCTTGCTCTGTGCAGAT-3'

All oligonucleotide primers were manufactured by Geneworks Pty Ltd. Primers were reconstituted with deionised and autoclaved water to a final concentration of 2000 μg/ml.

EXAMPLE 3

Genotype Determination

A 405 base pair DNA fragment (spanning nucleotides 1840-2245 of GenBank Accession No. Z48484; SEQ ID No. 1) of the tPA gene was amplified using the sequence-specific primer polymerase chain reaction method (PCR-SSP) as described in Bunce, M., C. M. O'Neill, M. C. Barnardo, et al. (1995) "Phototyping: comprehensive DNA typing for HLA-A, B, C, DRB1, DRB3, DRB4, DRB5 & DQB1 by PCR with 144 primer mixes utilizing sequence-specific primers (PCR-SSP)" *Tissue Antigens* 46(5): p. 355-367.

The specificity of PCR-SSP is derived from matching the terminal 3'-nucleotide of a primer with the target DNA sequence. Successful amplification by Taq polymerase during the PCR cycle will therefore only occur when matching between primer and DNA template (including the polymorphic nucleotide) occurs. Using this principle, oligonucleotide primers can be specifically tailored to incorporate a matching terminal 3'-nucleotide for a polymorphic site. A consensus primer that is complimentary to a stable, non-polymorphic region approximately 300-400 base pairs up or down stream in the DNA sequence allows for the amplification of a segment containing the single nucleotide polymorphism (snp). Under pre-specified PCR conditions, the amplification of the target DNA segment only occurs when both allele-specific and consensus primers are complimentary to the DNA template. The presence or absence of the snp can therefore be determined by detecting the PCR products using gel electrophoresis and visualization by ethidium bromide incorporation. PCR-SSP works because the Taq polymerase is deficient in exonuclease activity and therefore is unable to repair a mismatched 3'-terminal primer nucleotide.

This methodology allows PCR multiplexing to be readily performed. Multiplexing involves the addition of two other primers in the same reaction mix that are complimentary to a different DNA site. In this study, two oligonucleotide primers giving rise to a 600 bp DNA fragment from the HLA-DRB3 gene were amplified in each PCR-SSP reaction as a positive control to discriminate between a failed and a negative PCR reaction. Without such a control, all homozygous results (i.e. negative reaction in wild-type allele) would be questionable. Another important feature of this method is that the primer design allows for multiple small volume PCR reactions (where each reaction is specific for an allele) to occur under the same PCR cycling conditions. Genotyping in this study was performed using a 96-well PCR plate.

(i) Reagents for SSP-PCR

| Reagent | Supplier |
| --- | --- |
| Ammonium Sulphate | BDH Laboratory Supplies |
| AmpliTaq DNA Polymerase, 5 U/μl | Applied Biosystems |
| Cresol Red Solution (10 mg/ml) | Fluka Applied Biosystems |
| dnTP's (nucleotides) | |
| Magnesium Chloride (25 mM) | Applied Biosystems |
| Trizma Base | Sigma Chemicals |
| Tween 20 | BDH Laboratory Supplies |

(ii) Oligonucleotide Primer Preparation

A primer stock containing the HLA-DRB3 positive control primers was made using the following protocol:

8 ml deionised and autoclaved water

50μl cresol red

20μl HLA-DRB3 forward primer

20μl HLA-DRB3 reverse primer

Cresol red is an acid-base colour indicator (turns pink) when exposed to acidic DNA and allows for the visual identification of DNA contamination. The control primer stock is dispensed in separate 1.5 ml eppendorf tubes together with an allele-specific and consensus primer to a final volume of 1 ml.

5 μl of each primer mix was then dispensed in separate wells of a 96-well PCR plate. 10 μl of paraffin oil was added to each well to minimise primer and reagent evaporation during PCR thermal cycling.

The primer reaction mix for the tPA −7351 C/T snp was produced as follows by mixing 10 μl of allele-specific primer, 10 μl of the consensus primer and 980 uo of the control primer stock.

(iii) Reagent Mixes

10× PCR Buffer
Disolve 40.568 g Tris Base in 400 ml autoclaved water
Adjust pH to 8.9 with concentrated hydrochloric acid
Dissolve 10.96 g ammonium sulphate in the above solution
Autoclave
Add 5 ml Tween 20 and autoclaved water to 500 ml 10× dnTP
60 μl 100 mM dATP
60 μl 100 mM dCTP
60 μl 100 mM dTTP
60 μl 100 mM dGTP
5760 μl autoclaved, deionised water.

TMDH Mixture
6 ml 10× PCR buffer
6 ml 10× dNTP
5.1 ml 25 mM Magnesium Chloride
6 ml autoclaved, deionised water The PCR solution was prepared using the following protocol:
100 μl TMDH
57 μl autoclaved, deionised water
0.85 μl AmpliTaq DNA Polymerase (5U/pl)
3 μl DNA 1 μg/μl 8 μl of DNA solution was then added to each well containing the allele-specific primers. A colour change (pink—mediated by cresol red) confirmed the presence of DNA in the PCR reaction mix.

(iv) PCR Thermal Cycling

PCR was performed using a PTC-200 Peltier Thermal Cycler (MJ Research)
The following PCR cycling parameters were used:
5 cycles of:
96° C. for 25 seconds,
70° C. for 45 seconds,
72° C. for 45 seconds;
21 cycles of:
96° C. for 25 seconds,
65° C. for 50 seconds,
72° C. for 45 seconds; and
4 cycles of:
96° C. for 25 seconds,
55° C. for 60 seconds,
72° C. for 125 seconds.

The SSP-PCR products were analysed on a 2 percent agarose gel and visualized by ethidium bromide incorporation. A high-resolution digital photograph was taken and the genotype by gene counting. An example of the products of amplification from three representative subjects is shown in FIG. 2. The upper amplified band is that due to amplification of HLA-DBR3. The lower amplified band is the tPA allele specific amplification product. In FIG. 2, Subject 76 is CC homozygous, Subject 77 is TT homozygous, and Subject 78 is CT heterozygous.

As a quality assurance measure, genotyping was performed by two independent investigators who were blinded to the origin of DNA. They found 100 percent concordance.

EXAMPLE 4

Statistical Analysis

Statistical analysis of data derived from the study was performed using Stata statistical software (Version 7.0, College Station, Tex., USA). The baseline characteristics between cases and controls were analysed using the chi-square test for categorical variables and the two-tailed t-test for continuous variables. The strength of association between tPA −7,351 C/T genotype and ischemic stroke was estimated by calculating the odds ratio (OR) and 95 percent confidence intervals (Cl). The relative strength of association of known risk factors was determined in a similar fashion. A bi-variate chi-square analysis was used to examine the relation between tPA −7,351 C/T genotype and each traditional risk factor. This identified the important confounding variables that were incorporated in to an unconditional logistic regression model, which allowed determination of the risk of ischemic stroke associated with the tPA −7,351C/T polymorphism. Finally, a multivariate analysis stratified for ischemic stroke subtype was performed. A two tailed p-value of <0.05 was considered significant.

EXAMPLE 5

Subject Selection

Two hundred and one (201) patients who were admitted with acute ischemic stroke to one of five major hospitals within metropolitan Adelaide, South Australia, were approached to participate in the study of which one hundred and eight two (182) (90.5%) agreed to participate. One hundred and thirty-seven patients (137) (75%) presented with their first ever ischemic stroke.

The diagnosis of ischemic stroke was made by a neurologist in accordance with the World Health Organization (WHO) definition (as described in Hatono, S. (1976) "Experience from a multicentre stroke register: a preliminary report" Bull WHO 54: 541-553) and on brain computerized tomography (CT) or magnetic resonance imaging (MRl). lschemic stroke was sub-typed using the Oxfordshire Community Stroke Project (OCSP) classification system (as described in Bamford, J., P. Sandercock, M. Dennis, et al. (1991) "Classification and natural history of clinically identifiable subtypes of cerebral infarction" Lancet 337(8756): 1521-1526) into four categories: (a) Total anterior circulation syndrome; (b) Partial anterior circulation syndrome; (c) Posterior circulation syndrome and (d) Lacunar syndrome. Stroke subtype was validated with the brain CT or MRl findings.

The control group comprised of 301 non-hospitalized subjects who resided in metropolitan Adelaide and did not have a personal history of cerebrovascular disease. Controls were selected via random sampling of the South Australian electronic telephone directory and matched with patients for age (within five-year strata) and gender.

Following informed consent, subjects were interviewed and demographic information was recorded. Cerebrovascular risk factors including hypertension, hypercholesterolemia, and diabetes were considered to be present if there was a reported history or the individual was receiving medical treatment for the condition(s) at the time of investigation. An electrocardiogram was undertaken to determine the presence of atrial fibrillation. Subjects were considered as smokers if they had smoked cigarettes or tobacco on a regular basis within the last five years. A history of stroke in a first degree relative was also recorded. The study was approved by the North West Adelaide Health Service Ethics Committee.

EXAMPLE 6

Demographic Characteristics and Prevalence of Risk Factors for Patients with Ischemic Stroke and Healthy Controls The demographic characteristics and prevalence of risk factors for cerebrovascular disease for 182 ischemic stroke cases and 301 controls are shown in Table 1. As the study matched cases and controls for age and gender, no differences were observed between the two groups for these variables. The study population was predominantly of Caucasian origin with the difference between cases and controls not achieving statistical significance. Of the known risk factors examined, atrial fibrillation was associated with the highest risk of ischemic stroke, with 23% of cases versus 3% of controls affected (OR 8.5, 95% CI 4.1-17.4). A history of smoking within the last five years (OR 3.1, 95% CI 1.9-5.2) and diabetes (OR 2.7, 1.6-4.4) were also found to be significantly associated with ischemic stroke. The prevalence of hypertension was higher in cases than controls, however the difference was not statistically significant. No association was observed between ischemic stroke and a history of stroke in a first degree relative or hypercholesterolemia (Table 1).

TABLE 1

Demographic Characteristics and Prevalence of Risk Factors for Patients with Ischemic Stroke and Healthy Controls

|  | Controls (n = 301) | Cases (n = 182) | Odds Ratio (95% CI) | p value |
|---|---|---|---|---|
| Age* (years) | 73.4 ± 11.6 | 73.6 ± 12 |  | 0.8 |
| Gender |  |  |  |  |
| Females | 134 (45) | 80 (44) |  |  |
| Males | 167 (55) | 102 (56) | 1.0 (0.7-1.5) | 0.9 |
| Ethnic Origin |  |  |  |  |
| Caucasian | 299 (99.7) | 178 (98) |  |  |
| Non-Caucasian | 1 (0.3) | 4 (2) | 6.7 (0.8-60.6) | 0.09 |
| Smoking |  |  |  |  |
| No | 271 (90) | 135 (74) |  |  |
| Yes | 30 (10) | 47 (26) | 3.1 (1.9-5.2) | <0.0001 |
| Hypertension |  |  |  |  |
| No | 164 (54) | 87 (48) |  |  |
| Yes | 137 (46) | 85 (52) | 1.3 (0.9-1.9) | 0.2 |
| Diabetes Mellitus |  |  |  |  |
| No | 268 (89) | 137 (75) |  |  |
| Yes | 33 (11) | 45 (25) | 2.7 (1.6-4.4) | <0.0001 |
| Atrial Fibrillation |  |  |  |  |
| No | 291 (97) | 141 (77) |  |  |
| Yes | 10 (3) | 41 (23) | 8.5 (4.1-17.4) | <0.0001 |
| Family History |  |  |  |  |
| No | 201 (67) | 122 (67) |  |  |
| Yes | 100 (33) | 60 (33) | 1.0 (0.7-1.5) | 0.95 |
| Hypercholesterolemia |  |  |  |  |
| No | 182 (60) | 117 (64) |  |  |
| Yes | 119 (40) | 65 (36) | 0.9 (0.6-1.2) | 0.4 |

*Age is expressed as a mean ± standard deviation
In other rows, the values denote the number of patients or controls affected followed by (in parentheses) the percentage of the total for that group

EXAMPLE 7

Prevalence of the tPA −7,351 Polymorphism among Patients with Ischemic Stroke and Healthy Controls Two stroke patients died prior to venous blood sampling, thus genetic analysis (as described in Example 3) could not be performed in these cases.

Table 2 shows the prevalence of the tPA −7,351C/T polymorphism (shown in FIG. 1) in the remaining 180 ischemic stroke cases and 301 controls. Among the control group, 46% were homozygous for the C allele (CC), 45% were heterozygous (CT) and 9% were homozygous for the T allele (TT). The respective genotype distribution in the ischemic stroke cohort was 41% (CC), 46% (CT) and 13% (TT). Although the prevalence of the CT and TT genotypes was higher in stroke cases than controls, this was not statistically significant on univariate analysis. After adjustment for known risk factors, the TT genotype was found to be a significant and independent predictor of ischemic stroke (OR 1.9, 95% CI 1.01-3.6, p<0.05).

TABLE 2

Prevalence of the tPA −7,351 polymorphism among patients with ischemic stroke and healthy controls

| tPA −7,351 C/T Genotype | Controls n (%) | Cases n (%) | Univariate | | Multivariate Analysis* | |
|---|---|---|---|---|---|---|
|  |  |  | OR (95% CI) | p value | OR (95% CI) | p value |
| CC | 137 (46) | 74 (41) | 1.0 |  | 1.0 |  |
| CT | 136 (45) | 83 (46) | 1.1 (0.8-1.7) | 0.5 | 1.2 (0.8-1.9) | 0.3 |
| TT | 28 (9) | 23 (13) | 1.5 (0.8-2.8) | 0.2 | 1.9 (1.01-3.6) | <0.05 |

*Multivariate model includes ethnic origin, hypertension, diabetes, hypercholesterolemia, family history for stroke, smoking and atrial fibrillation

EXAMPLE 8

Distribution of the tPA −7,351C/T Genotypes among Patients Stratified for Stroke Subtype and Controls The distribution of the tPA −7,351C/T genotypes among patients stratified for stroke subtype and controls is shown in Table 3. Forty-four (24.5%) of ischemic stroke patients were classified with lacunar stroke. In this sub-group, the TT homozygous state was significantly associated with lacunar stroke on univariate analysis (OR 2.6, 95% Cl 1.1-6.4, p<0.05). Adjustment for known risk factors using an unconditional logistic regression model did not alter the significance of this finding (Table 3). Although the CT genotype did not show a statistically significant association with lacunar stroke, a dose-dependent effect for possession of the T allele and stroke risk was observed (CC OR 1.0, CT OR 1.1, TT OR 2.7). In contrast, no association between the tPA −7,351C/T genotypes and risk of non-lacunar stroke was observed.

IU/ml), endothelial cell growth supplement (150 μg/ml), L-glutamine (2 mM), penicillin (100 IU/ml) and streptomycin (100 μg/ml).

(iii) HeLa Cells

HeLa cells may be grown in DMEM supplemented with HEPES (20 mM), fetal bovine serum (heat-inactivated; 8% v/v), L-glutamine (2 mM), penicillin (100 IU/ml) and streptomycin (100 82 g/ml).

All cell types may be grown at 37° C. under a 5% $CO_2$/95% air atmosphere, and the medium replaced every 2-3 days. Subcultures may be obtained by trypsin/ethylenedinitrilotetraacetic acid disodiumsalt-dihydrate (EDTA) treatment at a split ratio of 1:3 for HUVEC and bovine aortic endothelial cells and of 1:10 for HeLa cells. Endothelial cells should be cultured for maximally three passages.

For experiments, confluent cultures will be used and the cells re-fed the day before the experiment with incubation

TABLE 3

Prevalence of the tPA −7,351 polymorphism among patients with ischemic stroke stratified for stroke subtype and healthy controls

| tPA −7,351 C/T Genotype | Control n (%) | Lacunar Stroke | | | Non-Lacunar Stroke* | | |
|---|---|---|---|---|---|---|---|
| | | n (%) | OR (95% CI) | p value | n (%) | OR (95% CI) | p value |
| CC | 137 (46) | 17 (39) | 1.0 | | 57 (42) | 1.0 | |
| CT | 136 (45) | 18 (41) | 1.1 (0.6-2.3) | 0.8 | 65 (48) | 1.3 (0.8-2.1) | 0.3 |
| TT | 28 (9) | 9 (20) | 2.7 (1.1-6.7) | <0.05 | 14 (10) | 1.7 (0.8-3.5) | 0.2 |

*Non-lacunar stroke defined as stroke patients presenting with either total anterior circulation syndrome, partial anterior circulation syndrome and posterior circulation syndrome. Odds ratios were determined by multivariate analysis that included ethnic origin, hypertension, diabetes, hypercholesterolemia, family history for stroke, smoking and atrial fibrillation.

EXAMPLE 9

Cell Culture (i) Bovine Aortic Endothelial Cells

Bovine aortic endothelial cells may be obtained by gently scraping the intimal surface of bovine thoracic aorta and may be maintained in Dulbecco's modified Eagle's medium-F-12 containing 10% fetal bovine serum (HyClone Laboratories, Logan, UT), 5 μg/ml deoxycytidine, 5 μg/ml thymidine, and 1% penicillin-streptomycin and Fungizone in culture flasks. The endothelial cells may be grown at 37° C. in a humidified 5% $CO_2$ incubator and used from passages 2 to 10. Endothelial cells may be identified by their typical morphology and by positive staining for 1,1-dioctadecyl-1-3,3,3',3'-tetramethylindocarbocyanine (di-I)-acetylated low-density lipoprotein (Biomedical Technologies, Stoughton, Mass.). Endothelial cells may be grown to confluence on culture plates coated with type I collagen.

(ii) HUVEC

Human umbilical vein endothelial cells (HUVEC) may be isolated by the method of Jaffe et al. (1973) *J. Clin. Invest.* 52:2745-2756 and cultured as described in Van Hinsbergh et al. (1987) *Arteriosclerosis* 7;389-400.

HUVEC may be grown on fibronectin-coated dishes in Dulbecco's modified Eagle's medium (DMEM) supplemented with N-2-hydroxyethylpiperazine-N'-2-ethanesulfonic acid (HEPES) (20 mM), newborn calf serum (heat-inactivated; 10% v/v), human serum (10% v/v), heparin (5 medium, i.e. for HUVEC: DMEM supplemented with human serum (10%), L-glutamine, penicillin and streptomycin; and for HeLa cells: DMEM supplemented with L-glutamine, penicillin and streptomycin.

EXAMPLE 10

Induction of Release of tPA from Endothelial Cells

HUVEC grown on 24-well plates may be washed with 3× with Krebs-Ringer-bicarbonate buffer (KRBH, 120 mmol/L NaCl, 4.75 mmol/L KCl, 1.2 mmol/L $KH_2PO_4$, 0.6 mmol/L $MgSO_4$, 1.2 mmol/L $CaCl_2$, 25 mmol/L $NaHCO_3$, and 25 mmol/L HEPES, pH 7.4)/BSA 0.1%, pH 7.4, preincubated for 30 minutes in 1 mL KRBH/BSA, and then incubated again for 30 minutes in 0.5 mL fresh KRBH/BSA alone, KRBH/BSA containing 1 NIH U/mL of human thrombin (Sigma), or KRBH/BSA containing 2 umol/L calcium ionophore A23187 (Sigma). The cell supernatants may be centrifuged and kept at −20° C. until determination of t-PA concentration.

EXAMPLE 11

Transfection of Endothelial Cells with tPA Upstream Region

The entire upstream region of the tPA locus (− to position +308) having either the wildtype sequence (−7351 C) or the polymorphic sequence (−7351 T) may be derived from the appropriate human genomic clones or by PCR amplification from genomic DNA.

The DNAs may then be fused to the chloramphenicol acetyltransferase (CAT) reporter gene. Transfection of endothelial cells with the tPA promoter-CAT gene constructs may be performed by employing the calcium phosphate precipitation method, incorporating a glycerol shock, as described in Sambrook, J, Fritsch, E. F. and Maniatis, T. Molecular Cloning: A Laboratory Manual 2nd. ed. Cold Spring Harbor Laboratory Press, New York. (1989). After 24 h, the transfected cells may be seeded on collagen-coated wells of plates and incubated overnight. After exposure to agents to induce tPA release (eg thrombin, calcium ionophore), cells may be harvested and relative changes in CAT activity quantitated by determining the percentage of [$^{14}$C]chloramphenicol converted to its acetylated products by thin-layer chromatography and liquid scintillation counting, as described in Sambrook, J, Fritsch, E. F. and Maniatis, T. Molecular Cloning: A Laboratory Manual 2nd. ed. Cold Spring Harbor Laboratory Press, New York. (1989).

The transfection efficiency may be evaluated by cotransfecting endothelial cells with cytomegalovirus promoter and lac Z gene construct. β-Galactosidase assay may be performed as described in Sambrook, J, Fritsch, E. F. and Maniatis, T. Molecular Cloning: A Laboratory Manual 2nd. ed. Cold Spring Harbor Laboratory Press, New York. (1989), and may be taken as a direct index of the efficiency of transfection and used to normalize CAT activities among various experiments.

EXAMPLE 12

Detennination of Release Rate of tPA in vitro

Cultures of human umbilical vein endothelial cells or bovine aortic endothelial cells may be grown to confluence as described above.

To determine the rate of release of tPA from endothelial cell, the medium may be replaced and tPA release induced (eg by the addition of thrombin, calcium ionophore), and the concentration of tPA present in the medium monitored with time by an enzyme-linked immunosorbent assay (ELISA) for the quantitation of total tPA (eg TintElize® t-PA, Biopool AB). The assays are based on the double-antibody principle.

To determine rate of release of tPA, the relative increase in the amount of tPA present in the medium with time may be calculated.

EXAMPLE 13

Testing Candidate Agents for Increase in Release Rate of tPA

Human endothelial cells having (i) the normal sequence in the tPA locus; (ii) one allele of the C to T mutation at −7351; or (iii) two alleles of the C to T mutation at −7351 may be obtained from human umbilical vein endothelial cells as described in Example 9. The HUVECs will be screened by genotype analysis to identify cells being homozygous for the normal tPA sequence, heterozygous for the C to T mutation at −7351, or homozygous for the C to T mutation.

The endothelial cells will then be cultured in the presence of a candidate compound for 1, 2, 4, 8, 12, 18 and 24 hours before induction of release of tPA. An appropriate concentration of the candidate compound will be selected for testing. As controls, the extent of release of tPA from endothelial cells in the absence of the compounds, and the extent of release of tPA from endothelial cells in the presence of monosodium [2-(6-hydroxynaphthalen-2-yl)-6-methyl-pyrimidin-4-yloxy]acetate dihydrate (JTV-926), will be tested. JTV-926 is an agent known to increase the release rate of tPA from endothelial cells (as described in Ueshima et al. (2002) "Function of tissue-type plasminogen activator releaser on vascular endothelial cells in thrombolysis in vivo" *Thrombosis Haemostasis* 87: 1069-74).

EXAMPLE 14

Determination of Release Rate of tPA in vivo

In vivo experiments of forearm t-PA release may be performed in healthy subjects as described in Jern et al. (1999) *Arterioscler. Thromb. Vasc. Biol.* 19(2): 454-459. Experiments may be performed after an overnight fast.

An arterial polyethylene catheter (Viggo Products, British Viggo) may be introduced percutaneously by the Seldinger technique into the brachial artery of the nondominant arm and advanced 10 cm in the proximal direction. An indwelling cannula (eg Venflon, Viggo) may be introduced retrogradely into a deep antecubital vein of the same arm for venous blood sampling from the muscle vascular bed.

Intraarterial blood pressure may be recorded continuously by an electrical transducer (eg EMT 35, Siemens-Elema) and a Mingograph 82 (eg Siemens-Elema). Mean arterial pressure may be obtained by electrical damping of the pressure signal. The electrocardiogram (ECG) may also be continuously monitored on the Mingograph. Venous occlusion plethysmography with a mercury-in-rubber strain-gauge may be used to assess FBF. FBF, in ml·min$^{-1}$·L$^{-1}$ tissue, and may be calculated from a number of separate recordings after each blood sampling.

After catheterization and application of recording devices, blood samples may be obtained twice 10 minutes apart at rest. Blood sampling procedures should be strictly controlled and standardized to avoid sympathoadrenal activation.

Arterial and venous blood samples may be drawn simultaneously by 2 persons from the catheters. The first 3 to 4 mL of blood will be discarded. Blood samples may be collected in tubes containing 1:10 0.45 mol/L sodium citrate buffer, pH 4.3 (eg Stabilyte, Biopool AB). Catheters may then be flushed with heparinized (5 IU/mL) saline after each blood sampling. The tubes should be kept on ice, and plasma isolated within 60 minutes by centrifugation at 4° C. and 2000 g for 20 minutes. Plasma will be immediately frozen and stored in aliquots at −70° C.

An enzyme-linked immunosorbent assay (ELISA) may be employed for the quantitative determination of total t-PA antigen (eg TintElize® t-PA, Biopool AB). The assays are based on the double-antibody principle. Free t-PA and t-PA in complex with inhibitors are detected with equal efficiency. The free, active fraction of t-PA (t-PA activity) may be determined by a bioimmunoassay (eg Chromolize(TM) t-PA, Biopool AB). Active t-PA is expressed in μg/L using the specific activity of 600 IU/μg. All samples from I individual will be assayed in duplicate on the same microtest plate.

Hematocrit may be determined in duplicate on arterial blood using a microhematocrit centrifuge (eg Hettich Hematokrit, Hettich Zentrifugen).

Net release rate of total t-PA will be determined as follows: venoarterial concentration gradients (AV-gradients) of each individual may be computed by subtraction of the plasma level of total t-PA measured in simultaneously collected venous and arterial blood. A positive difference indicates a net release and a negative net uptake. Individual forearm plasma flow may be calculated from FBF and arterial hematocrits corrected for 1% trapped plasma. Individual net release or uptake rates may b calculated from the AV-gradient times plasma flow per unit of time and L forearm tissue. The following formulas will be used:

FPF=FBF×([101-hematocrit]/100)

Net release=($C_V$−$C_A$)×FPF;

where $C_V$ denotes venous plasma concentration, and $C_A$ denotes arterial concentration.

Forearm net increment of active t-PA may be calculated with the same formula as net release of total t-PA. However, as regards active t-PA, local net flux may not only reflect tissue release/uptake but also possible shifts between the complex-bound and free fractions of t-PA on passage through the forearm vascular bed. To signify this fact, the term net increment is used instead of net release for active t-PA.

Finally, it will be appreciated that various modifications and variations of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are apparent to those skilled in the fields of vascular biology, molecular biology or related fields are intended to be within the scope of the present invention.

The invention claimed is:

1. A method of identifying a subject predisposed to ischemic stroke, wherein said method comprises:

determining the presence of a mutation in the subject that reduces the release rate from endothelial cells into the circulation of tissue plasminogen activator (t-PA), wherein said mutation is a cytosine to thymine mutation at position -7351 of the upstream region of the human tissue plasminogen activator locus, which is position 2228 of SEQ ID NO:1.

2. The method according to claim 1, wherein the ischemic stroke is a lacunar stroke.

3. The method according to claim 1, wherein the mutation is located in both alleles of the tissue plasminogen activator locus.

4. The method according to claim 1, wherein determining the presence of the mutation includes detection of the mutation by hybridization of nucleic acid isolated or derived from the subject to a reporter nucleic acid.

5. The method according to claim 1, wherein determining the presence of the mutation in the subject thereby (i) indicates that the subject is suitable for ischemic stroke interventive therapy; and/or (ii) indicates the risk of ischemic stroke occurring in a subject.

* * * * *

SEQUENCE LISTING

<160> NUMBER OF SEQ ID NOS: 6

<210> SEQ ID NO 1
<211> LENGTH: 9781
<212> TYPE: DNA
<213> ORGANISM: Homo sapiens

<400> SEQUENCE: 1

```
ggatcctctt atctcagcct cccaagtagc tggaccacag gagcaaacca ccatgcctgg      60
ctaattttct gtattttttt gtaaagatga ggtgggtctc actctgttgc ccaggctgat     120
cttgaactcc tggcttcaag caatccctca ccttgaactc ctaaagtgct gggattacag     180
gtgtgagcca ccttgcccag ctcacttctg taataagttg agagagaggt atatatagag     240
agaccacagt cacataactt ttattacagt accttgttat gattgttcta ttttactatt     300
ggttattgtt gttagtctct tgctgtgcct aatttataca ttaactttgt tttgttttgt     360
tttgttttgt ttttgagaca cggtctcact ctgtcaccta ggctggagtg cagtggcacg     420
atctcggctc acttcagtct tcgcctcctg gattcaagct attctcatgc ctcagccttc     480
cgagtagctg ggactacagg cacacaccac cacacccggc taagtttttt gtattttttag     540 tagagacagg gtttcatcat gttgcccagg ctggtctcca acggctgacc tcaagtgatc     600
cacctgcctc ggcctcccaa agtgctggga ttacaggcat gagccaccat gcctggccac     660
attaaccttg atcataggta tggatgtgta gggaagagca tcgtatatat agtgctcggt     720
actacccaca gattcaggca tccattggga tcttggaaca catccttgtg gttaaggggg     780
atgaccatgt gtgatggccc tcccagctcc ctgcctcctg ctcctggagt ctccatggct     840
cctcagcgcc aatcctccct gtctttcagc cctttgccct gtcagcctag actcaatgac     900
ccattgtgaa ccattaccac gatgcccgtt gacatgctgg aaactcttcc cttcttattc     960
taaaccccaa ggccctgtca acacgctcta ctggggaagc acacctactg ctttggtttc    1020
caatatgatt tcagagcaat tgccttgcaa accttcagca caacctctc ctgtgctgtt     1080 aacccttttga aagagtgtgc atttttaaaa agttggcatt gggcacagtg gctgaagcct    1140
gtatcccagc actttgggag gccgaggcag gtggatcacc tgaggtcagg agttcgagac    1200
cagcctggcc aacatggcaa aaccccgtct ctactaaaaa tacaaaaatt agctgggcat    1260
ggtggtgggc acctgtaatc ccagctactc gggagggtga ggcaggagaa tcacttgaac    1320
ccaggaggca gaggttgcat tgagccgaga tcgcatcact gcactccagg cagggtgaca    1380
gagcaagact ctgtctcaaa aaaaaaaaaa aagttggcat caatgtgttc ttccatctga    1440
tttatgtctt cacattacag catgttttct gtatgagccc acacatatca gatggtaact    1500
ttagaatggg tgggtctgtg ccattgtccc ggcacagctg tgagggtggt gacaggcagg    1560
tcagcaggtg cgtacagagg ggctttcttc tacattggag ttcaggtcgg atgatccagg    1620
```

-continued

```
tccacagtgt tcattcaggg ctctgtgttc tggtggcttc cgttgatttc taataaaagc    1680
tgcagactga gccagtcctg cacacacagg gagataggac aacgaacatt tgggatgtga    1740
ttaagcccat caatccaatc ggtgactaaa atcagacagg aagccctgtg ccccttagat    1800
aaagaaagcc tggggggaaa atgatctcaa gttcatttcg attggcgcaa actcctcaca    1860
gaggaaaaaa tgtacagtta gagtgaagtg aaagaacatc tctataaaat atgcatcact    1920
tcctggcggg gaggagagag gagctatgga aagctacacc aaagctgtat tcactggaca    1980
aaaatgcttg actcaggaag gaggccggag cggcgagtcc tgtgatgcca tggcgggagg    2040
tgggtcccat gtaaacagtg gtgttcctgt caccctgagc acatgcagtc tcccgtgggt    2100
aaccagaact gatgcaagag cccctgctgt ggaagtcacc acgctctccc agaacgcgcc    2160
tccccccagg tctgagtgat ctcattgccg aggtgaatag ggctttggcc gctctcccaa    2220
aggagcccgc cccagacaca gccatggcct gggactctgg ggtcaccctg gggtcagaag    2280
gaattatctg tattcacttg gttttggtta ttgtcagtgt tatttatgtg tttatttatt    2340
ttttattttt agagacaggc ttttactctg tctcccaggc tggagtgcag tgatgggatc    2400
acagttcact gcaacctcaa attttcaggt tcaagggatc cttccacctc agcctcctaa    2460
gtagctggga ctacatgcat gtgccaccac acctgactaa tttttttaatt atttgtagag    2520 ataggtctc gccatgttgc ccaggctggt ctcaaacttc tgggctcaag gaatcctccc    2580
accttggcct cccaaagtgt taggattaca ggagtgagcc acctcacctg gcctggtgtt    2640
gttattttaa aacaagaaaa gaaatgacca gaaaggctga aaggaaacac gcaccatcct    2700
ccataggagg ctgcaagggt tggtggcacc aggtccagaa gaagaagggc tcatagagca    2760
gaaaccagag cttgagcacc acctgggtgg catttggaag tgcctcagca cagccacttt    2820
gcagagtttg cacatttaaa ataaggagta ggctgggcac agtggctcat gcctgtaatc    2880
tcagcacttt aggaggccaa ggcaggcgga taccttgagt tcaggagttc gagaccagcc    2940
tggccaacat ggtgaaaccc cgtctctata aaaaaatat ataaaaatta gccaggcgtg    3000
gtggtgtgtg cctgtagtcc cagctactca ggaggctgag gtgagagaat cacttgaact    3060
ggggaggtgg aggttgcagt gagccaagat catgccactg cacttcagcc tgagcaatag    3120
agtgagatcc tgtctcaaaa aattaattaa ttaagttaaa taaagagtag cgcaattttc    3180
ctaaacagat tgaccagaga caccttaaaa attatacgac tgtgatagaa ttcctacaga    3240
tattcattag ctatgatatg ttggataaat aagcagatgg cagtgaatat tcttacagac    3300
caaatatttc tgcaaataaa attaaattct tatgtaaaat atgcatacat aaatatattc    3360
tagatataat tttataatat cagaaatgat catattttc atttgcaagt actttcttct    3420
ttttattttt agagttgggg gtcttgctct gttgcccaag ctgtactgca gtggcatgat    3480
gatagctcac tgcagccctg gactcctggg ctgacgtgat ctgcctgccc cagcctcctg    3540
aatggttttt tctttttttt gagacggagt ttcactcttg ttgcccaggc tggagtgcag    3600
tggcgcgatc tcagctcaca gcaacctcca cctcccaggt tcaagccctg aatggctttt    3660
taaaaatatt ttctcagagt cagggtcttg ctctgttgcc cagactggtc tcaaactcct    3720
gggttcaagc gatccccctg tcttggcttc ccaaagtgct gggattatag atgttagcca    3780
ctgcctcctg tcaatatttt ttaaattaat agacattcct tagagcagtt tcaggtttac    3840
agaaaaattg agcaggaagc acagagttcc catattatta tcccttctct tccctccgca    3900
gtttcccctg ttattatctt gtacttagtc cagtgatatt gtttttttt taaactacta    3960 ttgttttttca gttttttagat agtcaaaaca aagttgtaga cctatcatta tcttgtatgg    4020
```

```
gaatttaaaa aatgtatttc actgggctaa tgtattagtc cgttctcatg gtgctgtaaa    4080
gaaatgccca agactgggta atttataaag aaaagagatt taatggactc acagttcccc    4140
atggctggca gagcctcagg aaacttacaa tcatggagga aggcacctct tcacatggcg    4200
gcagaagaca gaatgagcac aaggaggga aatgctagac gataataaaa ccatcagatc     4260
tcatgagact cacagcttgg ggaaaaccgc cttcgtgatg caattacctc cacctgtttc    4320
tgcccttgac ctgtagggat tatggggatt aaaattaaag gtaagatttg ggtggggaca    4380
cagagccaaa ccatatcaac taaatattca aaaaaagtac tgctctaaga gagtacttca    4440
atttttaact tggtagcctt ggttcttgtt catgtgtgta acactaacat agcttaggag    4500
gcagttggaa aaaatttgag tcagggctc tttaaagttc ctttcttcat ctttgagaaa     4560
acagtacgag gctttccctt gcaaagttct ttccatcttt acttctctta tctgaaacgc    4620
aaggaaccta tagcttatca aaggtaaatg gactggacca gagtcgtgca actgacctca    4680
gaggagagaa aggaaacttt ctgacttcca accccaggct cattccagta gcctgcacat    4740
tcaccacggg ggtgtatttg aagattgata gctggcgatg tgttaggagg ctcaaaagag    4800
gtagatttag gagcagagaa agaaagttct gtgtcggaga atcagcaaac caacctgaga    4860
aactcaactc actccacaaa ggaattgatt gaaaattaga tgtgttcaaa ataacttga    4920 ataaactcat ggatactcca tcataagtta ttaaggaaaa ttcctattct tctgacacgc    4980
ttccatgaac aaccaggtcc ttccagtgcc agagagagag tgttgggctg ggcacaccca    5040
gtgtggagcc agtacatcta ctttttatgaa agtcatttag aagcatcact aaaggaactg    5100
aaaaacaatt caccaataat gacagtactc caacacctag ttttatcttc taatctctat    5160
ccatacatct atgtagtgtt tatattatta ttatttttg agatggagtc tcactcttgt     5220
tgcacgatct tggctcactg caacctccac ctcccaggtt caagtgattc tcttgcctca    5280
gcttcccgag tagcggggat tacaggtgcc cgccaccatg cctgactaat ttttgtgttt    5340
ttagtagaga tgggggtttca ccatgttggc caggctggtc tcgaactcct gatctcaagt    5400
gatttgcctg cctcggtctc ccaaagggct gggattatgg gtgtgagaca ccatgcctga    5460
tctacattat ttatatcaca gctcatgtac aaatttattt tcttcttctt ttgggcaagg    5520
caattttatg atttattttg gtatgtcggt ataattatgt tatcagtcat ctcaatggct    5580
acacaatatt gcagtattct aacatgtcct agtctactag gcccctatgt tttgacatct    5640
aagttatttt cagtatttag acagtcaaaa caatgttgaa tacttatcat tatcttgtat    5700
ggggatttaa aaaatgcatg tcagcaggct aaatattcaa aaattactgc tccaagaaaa    5760
taatccaatt tttaacttaa tattttgaaa taatttcaaa cttaccaaag agttgcaaga    5820
ataaagacct cctcctacag tttggtgaac agctcttaac aagaataaga tttgtaagag    5880
tccttcccat gccttcagct tgtcctgttt tgatgtttct cattgtttgt gtggaattca    5940
cacaactggt gctgttacca ccatgggcgt ctagtctgga tcagtggtcc tcagtctttt    6000
ttgcaccagg gaccagttttt gtaaagatag cttttccacg gacagaggga ggggagatag    6060
tttcgggatg attcaagagg attacattta ttgtgcactt tatttatatt actattacat    6120
tgtattatat aatgaaataa tggtatgact cagcataatg tagaatcagt gggaaccctg    6180
agcttgtttt cttataacta gatggtccca tctgggggtt atgggagaca gcgacagatc    6240
atcaggcatt agattcttat aaggagtgca aacctcaat ccctcgcatg tacagttcac     6300
aatagggttt gcactcctat gagaatctag tgccactgct gatccaaccg gaggtgcagc    6360
```

```
tcaggcagta atgcgagtga tggggagcgg ctgtaaacac agatgaagct tcactggctc    6420
tccagccact cacctcctgc tgcgcagcct ggttcctaac aggccacgga cagataccag    6480
cccatggccc cagggccggg gattcccagt ctagatggag acctagacaa ggcgtgcgac    6540
aataacaccg atttagatc catcatgaca tttaccccat cccctgcaaa gccagatggc    6600
taccaaaatt aaatcttagt ttagacacag aatgtccgtc ttctggtcca aaacatcctt    6660
gtcataagtt tcttggctgg gcgcggtggc tcacacctat aatcccagca ctttgggagg    6720
ctgaggcagg tggatcacga ggtcggggt ttgagaccag cctgaccaac atggtgaaac    6780
cccgtctcta ctaaaaatac aaaaaaatta gctgggcgtg gtggcgggca cctgtaatct    6840
cagctactca ggaggctgag gcaggagaat tgcttgaacc tggtggaggt tgcagtgagc    6900
cgagatcaca ccactgcact ctagcctggg cgacagagca agactctgtc tcaaaaaaaa    6960 aaaaagaaa ataaaaaaaa aaaacaagt tcttgccca ctcttccttt ctctgagttt    7020
ccagagacat cacatcattt cttacccagc tgagcagagt cccagcatgg ctctcgttcg    7080
aatacccatc ctgccacctg ccccagtgag aagggttgga gcagcccctg ttctctgccc    7140
ccgccacctc catgactcat gcattctgtg ggggaggcgc ccactgcaga acagccagg    7200 ctggctggga aaagccctgc agcaattccc cgtccagttt ctctgtgccc actttgtctc    7260
cgtgttatct aggcctggat ttatttctct ttttgaaaa tgaagggctt tgatgaaatg    7320
ttcacaggat gtgaggtcac caagatttt ttccttttt tctgttcttt tcttttcctc    7380
gaagtgatcc cttgactaaa atcaaggctc ccattgtcac cttatcagcc tgcccatgcc    7440
taattctgca ttctcaggct tccccagaat ctgtccgagg gaaaccaatc tcaattcaga    7500
aggaacacag aggccccagt ttctagggct gcaggatatt gctgggtctt aatcattcgg    7560
gtatatttca gcaaagctca gggcccctgc taatgatctg caaaccctct cctctcagtc    7620
tcccgttgtt tagcccctat ttataagtga gtgcatgtgg ttgttcactt tctgtttctg    7680
agttatttca gttaggataa tggtctccag tttcatccat gttgctccaa aagacagact    7740
tcattgtttt ttacggcttt gtcgtattcc tcggtgtata tgtgcatttt ctttatccag    7800
tcctccattg atggacactt aggttaattc tgtgcctttg ctattgtgaa ttgtgctgtt    7860
gtgaattgtg tgtgataaac gtgtgagtgc aggtgtcttt ttgatgtaat gatttctttt    7920
tctttgaata gatactcagt agtgggattg ccgggtcaaa tggatgttct attttagtt    7980 tgggaaatct ccatattgtt ttccatagag gttcaggatc caggatttaa gtgcaaccat    8040
tcagtggaaa accatcctct caagagttca atgagagtc ctcatgacca gcactccctg    8100
ctgaacggca atgccccacc ccccaaaaaa gcctccatcc tcaccatctt agaccacatt    8160
gcaggaaagc agcccatgc ccaccagaca ggcccacagc tgctgctgct catgggaggt    8220
ctacctcccg tgctcagcag gcaacccacc ccagtgcccc ttttctacaa tgaccatcag    8280
cagggctgca gcttcataaa aatgtgaaaa acagtttgaa agcaatgtga aaagcagtta    8340
ggtgcctttc aacttcaaac tcagcactca tggtttgaca aatatgagta tatttaggat    8400
cagaatgtat gaaatctggc ctctcctgaa tagtcggtca tcccacaatt tcctctgcca    8460
aacttctctt ccctccctgc gttctttctt tcacctctct ctcatttta caaggtctgg    8520 tctcagccag acatgaacca atgatgatag atgctcctgc tgagccctgt gatgtgccag    8580
ggccctgaca tgcgtggctt ctctctgatc ctcacgtgac ctgcagatgc aaaagccaga    8640
gctcagcata gttgaaaatc ttgattgagg tcatatccca gttactggca cagccggatt    8700
taaacctaag actttcccct acacgacagg gcttttattt ctcagtcatc tgaaaaggtg    8760
```

```
tcagcaaggg aaatggcttg tctatttcca ggggcatttt acaagcaaat actgaaaggc    8820
ttcggtgggc ttaagggctg atggctttga tcgaattkca ggcatgttgg ccccaaggcc    8880
ctgtgtatat tccctgggcc cactcaaggg gatgctggag ccggaaagtc cccggaggcc    8940
acctactgca gccctgcact ttacaaagaa gagaaagatt ctccctaaaa ttacagaaca    9000
gggccaaaga tgcctaccgg agcaaacccc catgggggca cctcctaccg caggtgagcc    9060
caaggctggt cctgccttct cagtggctac cccctgagc tcccgcacca cacaaagtgt     9120
tccaatcctt gtgcatcctc cagtccttt aacctctcat gtcctgagag gccagagcta    9180
cagccacaga ttccagaaga cacccactc ccagcccaa cctgctgcct ttagaattat      9240
aaacacttct tgtcatcaca gggtcctgaa agtccctttt aagcctggga cactaggact    9300
ctaaaggaag atgattctta aggtcccatc ccacttccaa attcctgcga ttcaatgaca    9360
tcacggctgt gaataatcag cctggcccga agccaggatg ggctgtgctg cttccaccgt    9420
gaacttcctc cccctgcttt ataaaaacag gcctgcctca gctccctcat ggccctgtcc    9480
actgagcatc ctcccgccac acagaaaccc gcccagccgg ggccaccgac cccaccccct    9540
gcctggaaac ttaaggaggc cggagctgtg gggagctcag agctgagatc ctacaggagt    9600
ccagggctgg agagaaaacc tctgcgagga aagggaagga gcaagccgtg gtaggtcggg    9660
tttctgtacc ttggggtctg tctcctcttc tttctcttaa aagtctttcc agcaagctga    9720
gccagtgaag gaatgcttta accaagggac caactttgta attcaggcaa ctagaggatc    9780
c                                                                    9781

<210> SEQ ID NO 2
<211> LENGTH: 20
<212> TYPE: DNA
<213> ORGANISM: Artificial Sequence
<220> FEATURE:
<223> OTHER INFORMATION: Consensus primer sequence used to amplify the
      region of the tPA locus

<400> SEQUENCE: 2
attggcgcaa actcctcaca                                                20

<210> SEQ ID NO 3
<211> LENGTH: 18
<212> TYPE: DNA
<213> ORGANISM: Artificial Sequence
<220> FEATURE:
<223> OTHER INFORMATION: WT primer sequence used to amplify the region
      of the tPA locus

<400> SEQUENCE: 3
atggctgtgt ctggggcg                                                  18

<210> SEQ ID NO 4
<211> LENGTH: 18
<212> TYPE: DNA
<213> ORGANISM: Artificial Sequence
<220> FEATURE:
<223> OTHER INFORMATION: SNP primer sequence used to amplify the region
      of the tPA locus

<400> SEQUENCE: 4
atggctgtgt ctggggca                                                  18

<210> SEQ ID NO 5
<211> LENGTH: 19
```

```
-continued

<212> TYPE: DNA
<213> ORGANISM: Artificial Sequence
<220> FEATURE:
<223> OTHER INFORMATION: Forward (sense) primer targeted to the HLA-DRB3
      gene

<400> SEQUENCE: 5
tgccaagtgg agcacccaa                                                    19

<210> SEQ ID NO 6
<211> LENGTH: 20
<212> TYPE: DNA
<213> ORGANISM: Artificial Sequence
<220> FEATURE:
<223> OTHER INFORMATION: Reverse (anti-sense) primer targeted to the
      HLA-DRB3 gene

<400> SEQUENCE: 6
gcatcttgct ctgtgcagat                                                   20
```